United States Patent [19]

Onodera et al.

[11] Patent Number: 5,276,178
[45] Date of Patent: Jan. 4, 1994

[54] PROCESS FOR PRODUCING METHACROLEIN AND METHACRYLIC ACID

[75] Inventors: Hideo Onodera; Shigeru Ohno; Ikuo Kurimoto, all of Himeji; Yukio Aoki, Taishi, all of Japan

[73] Assignee: Nippon Shokubai Co., Ltd., Osaka, Japan

[21] Appl. No.: 721,574

[22] PCT Filed: Dec. 6, 1990

[86] PCT No.: PCT/JP90/01594
§ 371 Date: Aug. 2, 1991
§ 102(e) Date: Aug. 2, 1991

[87] PCT Pub. No.: WO91/08185
PCT Pub. Date: Jun. 13, 1991

[30] Foreign Application Priority Data

Dec. 6, 1989 [JP] Japan ............... 1-315163
Dec. 28, 1989 [JP] Japan ............... 1-338471
Jan. 18, 1990 [JP] Japan ............... 2-7200
Jan. 26, 1990 [JP] Japan ............... 2-14815

[51] Int. Cl.$^5$ ............... C07C 51/16; C07C 51/00
[52] U.S. Cl. ............... 562/537; 562/538; 562/546; 562/599
[58] Field of Search ............... 562/537, 538, 546, 599

[56] References Cited

U.S. PATENT DOCUMENTS

| | | | |
|---|---|---|---|
| 4,001,317 | 1/1977 | Grasselli et al. | 260/533 N |
| 4,148,757 | 4/1979 | Brazdil et al. | 252/432 |
| 4,323,520 | 4/1982 | Hardman et al. | 260/465.9 |
| 4,329,513 | 5/1982 | Aoshima et al. | 568/492 |
| 4,354,044 | 10/1982 | Aoshima et al. | 568/479 |
| 4,438,217 | 3/1984 | Takata et al. | 502/205 |
| 4,511,671 | 4/1985 | Saito et al. | 502/242 |
| 4,558,028 | 12/1985 | Tsuneki et al. | 502/211 |
| 4,816,603 | 3/1989 | Oh-kita et al. | 562/538 |
| 4,837,360 | 6/1989 | Kadowaki et al. | 562/546 |
| 5,208,371 | 5/1993 | Kuoda et al. | 562/538 |

FOREIGN PATENT DOCUMENTS 0168826 7/1985 European Pat. Off. .
2114414 10/1971 France .
1529384 2/1976 United Kingdom .
2063861 6/1981 United Kingdom .

Primary Examiner—José G. Dees
Assistant Examiner—Porfirio Nazario
Attorney, Agent, or Firm—Sherman and Shalloway

[57] ABSTRACT

The present invention provides a process for producing methacrolein and methacrylic acid by subjecting at least one material selected from isobutylene, t-butanol and methyl t-butyl ether to gas phase catalytic oxidation with molecular oxygen or a molecular oxygen-containing gas using a fixed bed multi-tubular reactor.

3 Claims, No Drawings

PROCESS FOR PRODUCING METHACROLEIN AND METHACRYLIC ACID

UTILIZATION FIELD IN INDUSTRY

The present invention relates to a process for producing methacrolein and methacrylic acid by using, as a starting material, at least one compound selected from isobutylene, t-butanol (tertiary butanol) and methyl t-butyl ether (methyl tertiary butyl ether) and subjecting the starting material to gas phase catalytic oxidation with molecular oxygen or a molecular oxygen-containing gas.

Prior Art

A number of proposals have been made on the catalyst used in production of methacrolein and methacrylic acid by the high-temperature gas phase catalytic oxidation of isobutylene and/or t-butanol. These proposals relate mainly to the selection of the components constituting the catalyst and their ratio.

The above oxidation reaction is a highly exothermic reaction. Therefore, in the reaction, heat build-up in the catalyst layer is large; particularly in the abnormally hot areas called "hot spots", product yield is low due to an excessive oxidation reaction and, moreover, deterioration of catalyst takes place owing to a high thermal load and catalyst life is influenced greatly. Accordingly, heat build-up in hot spots is a serious problem in the industrial practice of the above oxidation reaction. This heat build-up in hot spots tends to be striking particularly when the concentration of material gas is made higher or the space velocity is made larger (such reaction conditions are hereinafter referred to as "high-load reaction conditions" in some cases) in order to enhance the productivity; as a result, the reaction conditions of the oxidation reaction are considerably restricted currently.

Hence, minimization of heat build-up in hot spots is very important for industrial production of methacrolein and methacrylic acid at high yields as well as for reduction of catalyst deterioration and resultant stable operation over a long period. Prevention of heat build-up in hot spots is particularly important in molybdenum-based catalysts because the molybdenum component causes easy sublimation.

Various proposals have hitherto been made in order to suppress heat build-up in hot spots. For example, Japanese Patent Publication No. 36740/1987 proposes the use of a ring-shaped catalyst. The document describes that the change of catalyst shape from spherical or columnar shape to ring shape in the molded catalyst conventionally used for oxidation of isobutylene or t-butanol can suppress heat build-up in hot spots and accordingly an excessive oxidation reaction, and is very effective for the improvement of product yield. This method certainly has an effect of reducing the thermal load for catalyst, but gives no sufficient results under high-load reaction conditions, in particular.

Also, a method in which catalysts of different activities are filled in a plurality of reaction zones formed by dividing the catalyst layer of reactor and in which an oxidation reaction is carried out in the reaction zones, is known in Japanese Patent Publication No. 38331/1988 for production of, for example, acrolein and acrylic acid from propylene.

Further, Japanese Laid-Open Patent Publication No. 127013/1976 discloses the use of a combination of a supported catalyst and a molded catalyst essentially of the same composition for production of unsaturated aldehydes and acids from propylene and isobutylene. The document shows, in Examples, specific cases of producing acrolein and acrylic acid from propylene, but discloses no specific case of producing methacrolein and methacrylicacid from isobutylene. Therefore, it is difficult to evaluate the effect of the above technique on the production of methacrolein and methacrylic acid from isobutylene.

In the reaction for producing methacrolein and methacrylic acid by subjecting isobutylene, t-butanol or methyl t-butyl ether to gas phase catalytic oxidation, all of these starting materials have a methyl group at the α-position unlike propylene; accordingly, there occur many side reactions caused by the presence of methyl group, such as parallel reactions, successive reactions and the like, producing a number of by-products in large amounts. For example, the heat generated in the reaction for producing methacrolein and methacrylic acid from isobutylene is larger than that for producing acrolein and acrylic acid from propylene; this aggravates the heat build-up in catalyst layer and promotes the formation of by-products by side reactions. Further, methacrolein is unstable as compared with acrolein and easily gives rise to so-called "post-reactions" such as autoxidation and the like, worsening the product yield.

As described above, the reaction for producing methacrolein and methacrylic acid by oxidation of isobutylene, t-butanol or methyl t-butyl ether is complex as compared with the reaction for producing acrolein and acrylic acid by oxidation of propylene, making it difficult to obtain intended products at high yields. Therefore, the application of the very techniques obtained in the production of acrolein, acrylic acid, etc. to the production of methacrolein and methacrylic acid has not been sufficiently effective, and further study has been necessary in order to develop a catalyst or process suitably used for production of methacrolein and methacrylic acid.

PROBLEMS THAT THE INVENTION INTENDS TO SOLVE

An object of the present invention is to provide a process for producing methacrolein and methacrylic acid at high yields by subjecting at least one material selected from isobutylene, t-butanol and methyl t-butyl ether, to gas phase catalytic oxidation.

Another object of the present invention is to provide a process for producing methacrolein and methacrylic acid by subjecting at least one material selected from isobutylene, t-butanol and methyl t-butyl ether, to gas phase catalytic oxidation, in which process heat build-up in hot spots in catalyst layer is suppressed to improve yields of methacrolein and methacrylic acid, prevent catalyst deterioration and enable long stable use of catalyst.

Still another object of the present invention is to provide a process for producing methacrolein and methacrylic acid by subjecting at least one material selected from isobutylene, t-butanol and methyl t-butyl ether, to gas phase catalytic oxidation under high-load reaction conditions, in which process heat build-up in hot spots in catalyst layer is suppressed to improve yields of methacrolein and methacrylic acid, prevent catalyst deterioration, enable long stable use of catalyst and enhance productivity significantly.

MEANS FOR SOLVING THE PROBLEMS

The present inventors found that the above objects can be achieved by preparing a plurality of particular molybdenum-based catalysts of different activities and filling the plurality of molybdenum-based catalysts into a plurality of reaction zones formed by dividing the catalyst layer of reactor into two or more portions, in such a way that the activity of filled catalyst becomes higher as a material gas proceeds from the inlet to the outlet. The present invention has been completed based on the finding.

The present invention relates to a process for producing methacrolein and methacrylic acid by subjecting at least one material selected from isobutylene, t-butanol and methyl t-butyl ether to gas phase catalytic oxidation with molecular oxygen or a molecular oxygen-containing gas using a fixed bed multi-tubular reactor, which process is characterized in that: (α) there are used, as catalysts, compound oxides represented by the following general formula (I)

(in the formula, Mo represents molybdenum, W represents tungsten, Bi represents bismuth, Fe represents iron, A represents at least one element selected from nickel and cobalt, B represents at least one element selected from alkali metals and thallium, C represents at least one element selected from alkaline earth metals, D represents at least one element selected from phosphorus, tellurium, antimony, tin, cerium, lead, niobium, manganese, arsenic and zinc, E represents at least one element selected from silicon, aluminum, titanium and zirconium, and O represents oxygen; a, b, c, d, e, f, g, h, i and x represent the numbers of atoms of Mo, W, Bi, Fe, A, B, C, D, E and O, respectively; when a is 12, b=0-10, c=0.1-20, d=0.1-20, e=2-20, f=0-10, g=0-10, h=0-4, i=0-30 and x=a value determined by the oxidation states of individual elements), (β) each reaction tube has a plurality of reaction zones formed by dividing the catalyst layer in the reaction tube into two or more portions in the axial direction of the tube, and (γ) the plurality of reaction zones are filled with catalysts shown in the above (α) having different activities, prepared by varying the types and/or amounts of the elements constituting the A group, B group, C group, D group and E group in the general formula (I) and/or with catalysts shown in the above (α) having different activities, prepared by varying the amount of at least one element of W, Bi and Fe in the general formula (I), in such a way that the activity of filled catalyst becomes higher as a material gas proceeds from the inlet to the outlet.

The present invention further relates to a process for producing methacrolein and methacrylic acid, characterized in that the above-mentioned plurality of reaction zones are filled with catalysts of different activities prepared by varying the types and/or amounts of the elements constituting the A group, B group, C group, D group and E group in the above general formula (I) and further by varying the firing temperature employed in catalyst preparation, and/or with catalysts of different activities prepared by varying the amount of at least one element of W, Bi and Fe in the general formula (I) and further by varying the firing temperature employed in catalyst preparation, in such a way that the activity of filled catalyst becomes higher as a material gas proceeds from the inlet to the outlet.

The present invention is hereinafter described in detail.

The starting material used in the present invention is at least one compound selected from isobutylene, t-butanol and methyl t-butyl ether, and is subjected to a reaction ordinarily in the form of a mixed gas further containing molecular oxygen, steam and an inert gas (e.g. nitrogen, carbon dioxide).

The catalysts used in the present invention are compound oxides represented by the above-mentioned general formula (I). The method for preparing the catalysts and the materials used therefor have no particular restriction, and the catalysts can be prepared by employing the method and materials generally used in the preparation of same type catalyst.

In the present invention, a plurality of catalysts of different activities, each represented by the general formula (I) are prepared and filled in a particular arrangement.

The catalysts of different activities can easily be prepared by varying the types and/or amounts of the elements constituting the A group, B group, C group, D group and E group in the general formula (I). That is, the catalysts of different activities can be obtained by varying the type and/or amount of at least one element selected from nickel, cobalt, alkali metals, alkaline earth metals, thallium, phosphorus, tellurium, antimony, tin, cerium, lead, niobium, manganese, arsenic, zinc, silicon, aluminum, tin and zirconium the [variation must be made within the atomic ratio specified by e, f, g, h and i in the general formula (I)].

The catalysts of different activities can also be obtained by varying the amount of at least one element of W, Bi and Fe [the variation must be made within the atomic ratio specified by b, c and d in the general formula (I)].

The catalyst of different activities can also be obtained by varying the types and/or amount of the above elements and further by varying the firing temperature employed in catalyst preparation. Specifically, the catalysts of different activities are prepared by varying the firing temperature (400°–600° C.) employed in catalyst preparation, so as to give a firing temperature difference of at least 5° C. between any two different catalysts.

The firing temperature employed in catalyst preparation in the present invention is, as mentioned above, 400°–600° C., preferably 450°–550° C.

When the firing temperature is lower than 400° C., no sufficient catalyst activity is obtained. Meanwhile, when the firing temperature is higher than 600° C., the resulting catalyst activity is low owing to the occurrence of sintering, etc. Therefore, such firing temperatures are not preferable. When the firing temperature difference is less than 5° C. between any two catalysts, the resulting catalyst activity difference caused by the firing temperature difference is insufficient between these catalysts; therefore, such a firing temperature difference is not preferable. The firing temperature difference need not be unnecessarily large and is generally 5°–100° C., preferably 10°–70° C.

In the present invention, the preparation of catalysts of different activities and the filling of the catalysts can be specifically carried out by the following embodiments.

(1) A plurality of catalysts of controlled activities are prepared by varying the amount of W element in the general formula (I), or by varying not only said amount but also the firing temperature employed in catalyst preparation. The thus prepared catalysts are filled into a plurality of reaction zones formed by dividing the catalyst layer or each reaction tube, in such a way that the activity of filled catalyst becomes higher as a material gas proceeds from the inlet to the outlet. In this case, the amount of W element used is preferably such that $b=0.001-10$ when $Mo=12$ in the general formula (I).

(2) A plurality of catalysts of controlled activities are prepared by varying the amount of Bi element in the general formula (1), or by varying not only said amount but also the firing temperature employed in catalyst preparation. The thus prepared catalysts are filled into reaction zones formed by dividing the catalyst layer of each reaction tube, in such a way that the activity of filled catalyst becomes higher as a material gas proceeds from the inlet to the outlet.

(3) A plurality of catalysts of controlled activities are prepared by varying the amount of Fe element in the general formula (I), or by varying not only said amount but also the firing temperature employed in catalyst preparation. The thus prepared catalysts are filled into reaction zones formed by dividing the catalyst layer of each reaction tube, in such a way that the activity of filled catalyst becomes higher as a material gas proceeds from the inlet to the outlet.

(4) A plurality of catalysts of controlled activities are prepared by varying the type and/or amount of at least one element selected from the A group elements in the general formula (I), or by varying not only said type and/or amount but also the firing temperature employed in catalyst preparation. The thus prepared catalysts are filled into reaction zones formed by dividing the catalyst layer of each reaction tube, in such a way that the activity of filled catalyst becomes higher as a material gas proceeds from the inlet to the outlet.

(5) A plurality of catalysts of controlled activities are prepared by varying the type and/or amount of at least one element selected from the B group elements in the general formula (I), or by varying not only said type and/or amount but also the firing temperature employed in catalyst preparation. The thus prepared catalysts are filled into reaction zones formed by dividing the catalyst layer of each reaction tube, in such a way that the activity of filled catalyst becomes higher as a material gas proceeds from the inlet to the outlet. In this case, the amount of the B group element(s) is preferably such that $f=0.001-10$ when $Mo=12$ in the general formula (I).

(6) A plurality of catalysts of controlled activities are prepared by varying the type and/or amount of at least one element selected from the C group elements in the general formula (I), or by varying not only said type and/or amount but also the firing temperature employed in catalyst preparation. The thus prepared catalysts are filled into reaction zones formed by dividing the catalyst layer of each reaction tube, in such a way that the activity of filled catalyst becomes higher as a material gas proceeds from the inlet to the outlet. In this case, the amount of the C group element(s) is preferably such that $g=0.001-10$ when $Mo=12$ in the general formula (I).

(7) A plurality of catalysts of controlled activities are prepared by varying the type and/or amount of at least one element selected from the D group elements in the general formula (I), or by varying not only said type and/or amount but also the firing temperature employed in catalyst preparation. The thus prepared catalysts are filled into reaction zones formed by dividing the catalyst layer of each reaction tube, in such a way that the activity of filled catalyst becomes higher as a material gas proceeds from the inlet to the outlet. In this case, the amount of the D group element(s) is preferably such that $h=0.001-4$ when $Mo=12$ in the general formula (I).

(8) A plurality of catalysts of controlled activities are prepared by varying the type and/or amount of at least one element selected from the E group elements in the general formula (I), or by varying not only said type and/or amount but also the firing temperature employed in catalyst preparation. The thus prepared catalysts are filled into reaction zones formed by dividing the catalyst layer of each reaction tube, in such a way that the activity of filled catalyst becomes higher as a material gas proceeds from the inlet to the outlet. In this case, the amount of the E group element(s) is preferably such that $i=0.001-30$ when $Mo=12$ in the general formula (I).

(9) At least 2 catalysts selected from the catalysts of controlled activities mentioned in the above (1) to (8) are filled into the reaction zones formed by dividing the catalyst layer of each reaction tube, in such a way that the activity of filled catalyst becomes higher as a material gas proceeds from the inlet to the outlet.

In the present invention, "activity" refers to the conversion of starting material.

Of the above embodiments, the method mentioned in the above (5) is preferable because it gives high conversion of starting material and high selectivities of intended products and, as a results, gives intended products at high yields. In the method mentioned in the above (5), use of a plurality of catalysts prepared by varying the type and/or amount of at least one element selected from the B group elements and further by varying the firing temperature employed in catalyst preparation, is particularly preferable because it causes no catalyst deterioration over a long period of time and gives intended products at high yields. In this case, the firing temperature in catalyst preparation is varied in the range of 400°-600° C. so that the firing temperature difference between any two catalysts of the plurality of catalysts becomes at least 5° C.

The tungsten component is effective for improvement of catalyst activity, and its use in combination with the B group element(s) gives a catalyst of significantly improved activity but of no reduced selectivity. The proportion of tungsten used is 0-10, preferably 0.5-10 when the proportion of molybdenum used is 12.

The methods specified by the present invention, described in detail above, i.e., the present methods for control of catalyst activity by variation of catalyst composition or by variation of not only catalyst composition but also firing temperature have made it possible to produce methacrolein and methacrylic acid at high yields over a long period of time. The present invention is presumed to have the following functions.

Control of catalyst activity is made possible by varying the chemical properties or physical properties or both of catalyst.

Control of catalyst activity by composition variation is believed to bring about variation of chemical properties of catalyst. Such variation gives rise to variation of catalyst adsorbability for starting material (isobutylene, t-butanol or methyl t-butyl ether), or variation of removability of products (methacrolein and methacrylic acid) from catalyst; thus, catalyst activity and selectivity are varied.

Meanwhile, variation of firing temperature is believed to contribute not only to variation of chemical properties (e.g. crystalline structure, stability) of catalyst, but also to variation of physical properties (namely, specific surface area, pore volume, distribution of pore diameters) of catalyst. It is believed that variation of firing temperature has made it possible to obtain a catalyst having physical properties most suitable for an intended reaction and, as a result, attain high yields.

In the reaction for producing methacrolein and methacrylic acid, a number of by-products are generated in a large amount, as mentioned previously. Hence, by preparing catalysts different in chemical properties and preferably even in physical properties, optimization of catalysts has been achieved, whereby high yields and longer catalyst life have been realized.

The catalysts used in the present invention can be made into molded catalysts by an ordinary molding method such as extrusion molding method, tablet molding method or the like, or into supported catalysts by allowing an ordinary inactive carrier (e.g. silicon carbide, alumina, zirconium oxide, titanium oxide) to support a catalyst component, i.e., a compound oxide represented by the general formula (I).

The types of a plurality of catalysts filled into reaction zones may be the same or different. When the number of the reaction zones is, for example, 2, it is possible to arrange a supported catalyst in a reaction zone also functioning as a material gas inlet and a molded catalyst in a reaction zone also functioning as an outlet.

The shapes of the catalysts used in the present invention have no particular restriction and can be any of spherical shape, columnar shape, ring shape, etc. The use of ring-shaped catalysts, in particular, can give various advantages such as prevention of heat build-up in hot spots, increased yield, prevention of catalyst deterioration, reduced pressure loss in catalyst layer, and the like. Therefore, ring-shaped catalysts can be preferably used in the present invention. The preferable dimensions of the ring-shaped catalysts are such that the outside diameter is 3-10 mm, the length is 0.5-2 times the outside diameter, and the inside diameter (the diameter of the through-hole formed in the length direction) is 0.1-0.7 time the outside diameter.

The shapes of a plurality of catalysts filled into reaction zones may be the same or different. When the number of the reaction zones is, for example, 2, good results are obtained by arranging a ring-shaped catalyst in a reaction zone also functioning as a material gas inlet and a pellet-shaped catalyst in a reaction zone also functioning as an outlet.

In the present invention, the catalyst layer in each reaction tube is divided into two or more portions in the axial direction of the tube to form a plurality of reaction zones. In these reaction zones are arranged a plurality of catalysts of different activities as mentioned above, in such a way that the activity of filled catalyst becomes higher as a material gas proceeds from the inlet to the outlet. That is, a catalyst of lowest activity is arranged in the reaction zone also functioning as a material gas inlet, and a catalyst of highest activity is arranged in the reaction zone also functioning as a material gas outlet. Such arrangement of a plurality of catalysts of different activities makes it possible to suppress heat build-up in hot spots and obtain intended products at high yields.

The larger the number of reaction zones formed by dividing the catalyst layer, the easier is the control of temperature distribution in reaction zones. However, 2 or 3 reaction zones can sufficiently attain an intended effect industrially. The division ratio cannot be specified in a particular range because it differs by the composition, shape, etc. to be possessed by the catalyst of each reaction zone. Desirably, the division ratio is appropriately selected so that the overall activity and selectivity become optimum.

The gas phase catalytic oxidation reaction of the present invention may be carried out by an ordinary single-pass method or a recycle method. The oxidation reaction can be effected under the conditions generally employed in similar reactions. For example, a starting material, i.e. a mixed gas consisting of 1-10% by volume of at least one compound selected from isobutylene, t-butanol and methyl t-butyl ether, 3-20% by volume of molecular oxygen, 0-60% by volume of steam, 20-80% by volume of an inert gas (e.g. nitrogen, carbon dioxide), etc. is introduced into the above-mentioned reaction zones at a temperature range of 250°-450° C. at a pressure of normal pressure to 10 atm. at a space velocity (SV) of 300-5,000 $hr^{-1}$ (STP).

In the present process, as compared with conventional processes, particularly excellent results can be obtained under high-load reaction conditions employed for higher productivity, for example, under the conditions of higher material concentration or higher space velocity.

EFFECTS OF THE INVENTION

In the present invention, various meritorious effects such as mentioned below can be obtained by filling a plurality of particular molybdenum-based catalysts of different activities into a plurality of reaction zones formed by dividing the catalyst layer in each reaction tube, in such a way that the activity of filled catalyst becomes higher as a material gas proceeds from the inlet to the outlet.

(a) Methacrolein and methacrylic acid can be obtained at high yields.

(b) Heat build-up in hot spots can be suppressed effectively.

(c) The excessive oxidation reaction in hot spots can be prevented, and intended methacrolein and methacrylic acid can be obtained at high yields.

(d) Catalyst deterioration due to thermal load can be prevented and stable use of catalyst over long period is possible.

(e) Intended methacrolein and methacrylic acid can be obtained at high yields even under high-load reaction conditions (e.g. high material concentration, high space velocity). As a result, significantly increased productivity can be obtained.

Further, the following effect can additionally be obtained by the use of ring-shaped catalyst.

(f) Pressure loss in catalyst layer is reduced, whereby electricity consumption can be lowered.

Thus, the process of the present invention is very useful for industrial production of methacrolein and methacrylic acid.

EXAMPLES

The present invention is hereinafter described more specifically with reference to Examples.

Conversion, selectivity and total per-pass yield are defined by the following formulas.

Conversion (mole %) = (moles of starting material reacted) ÷ (moles of starting material fed) × 100

Selectivity (mole %) = (moles of methacrolein or methacrylic acid formed) ÷ (moles of starting material reacted) × 100

Total per-pass yield (mole %) = (moles of methacrolein and methacrylic acid formed) ÷ (moles of starting material fed) × 100

EXAMPLE 1

1,456 g of cobalt nitrate and 202 g of ferric nitrate were dissolved in 1,000 ml of water. 243 g of bismuth nitrate was dissolved in an aqueous nitric acid solution consisting of 30 ml of concentrated nitric acid and 120 ml of water.

Separately, 1,059 g of ammonium paramolybdate and 265 g of ammonium paratungstate were dissolved in 3,000 ml of water with heating. To the resulting aqueous solution were dropwise added the above prepared two aqueous solutions, and mixing was carried out. Thereto were added an aqueous solution obtained by dissolving 68.3 g of cesium nitrate in 200 ml of water, and 203 g of silica sol of 20 weight % concentration in this order, and mixing was carried out.

The thus obtained suspension was stirred with heating, and subjected to evaporation to dryness. The residue was molded into pellets of 6 mm in outside diameter and 6.6 mm in length. The pellets were fired at 500° C. for 6 hours in an air stream to obtain a catalyst (I). This catalyst (I) had the following composition in terms of atomic ratio excluding oxygen.

$Mo_{12}W_2Bi_1Fe_1Co_{10}Cs_{0.7}Si_{1.35}$

A catalyst (2) was prepared in the same manner as in the preparation of the catalyst (I) except that the amount of cesium nitrate was changed to 9.8 g. This catalyst (2) had the following composition in terms of atomic ratio excluding oxygen.

$Mo_{12}W_2Bi_1Fe_1Co_{10}Cs_{0.1}Si_{1.35}$

With respect to the activities of the catalysts (1) and (2), the catalyst (2) has a higher activity than the catalyst (1), as is clear from the results of Comparative Examples 1 and 2 shown later.

750 ml of the catalyst (1) was filled into the material gas inlet portion of a steel-made reaction tube of 25.4 mm in diameter, and 750 ml of the catalyst (2) was filled into the material gas outlet portion.

A mixed gas of a composition consisting of 6% by volume of isobutylene, 13.2% by volume of oxygen, 10% by volume of steam and 70.8% by volume of nitrogen was introduced from the inlet of the reaction tube, and a reaction was carried out at a reaction temperature of 340° C. at a space velocity (SV) of 1,600 hr$^{-1}$. The results are shown in Table 1.

COMPARATIVE EXAMPLE 1

A reaction was carried out in the same manner as in Example 1 except that no catalyst (2) was used and only the catalyst (1) (1,500 ml) was filled. The results are shown in Table 1.

COMPARATIVE EXAMPLE 2

A reaction was carried out in the same manner as in Example 1 except that no catalyst (1) was used and only the catalyst (2) (1,500 ml) was filled. The results are shown in Table 1.

COMPARATIVE EXAMPLE 3

A catalyst (3) was prepared in the same manner as for the catalyst (1) of Example 1 except that the amount of cesium nitrate was changed to 39 g. This catalyst (3) had the following composition in terms of atomic ratio excluding oxygen.

$Mo_{12}W_2Bi_1Fe_1Co_{10}Cs_{0.4}Si_{1.35}$

A reaction was carried out in the same manner as in Example 1 except that only the catalyst (3) (1,500 ml) was filled into the reaction tube. The results are shown in Table 1.

It is appreciated from the results of Example 1 and Comparative Examples 1–3 that the catalyst (1) has a very low activity, the catalyst (2) has a high activity, and both of them give a low total per-pass yield while the catalyst system of the present invention which is a combination of the catalysts (1) and (2), gives a high total per-pass yield and produces intended methacrolein and methacrylic acid at high yields.

When the catalyst (3) having a composition intermediate between those of the catalysts (1) and (2) is compared with the catalyst system of the present invention which is a combination of the catalysts (1) and (2), the catalyst (3) gives a low total per-pass yield and a very large temperature difference (a very large ΔT) between the reaction temperature and the hot spots temperature. Therefore, it is thought that catalyst deterioration due to thermal load is striking in the catalyst (3). Accordingly, it is appreciated that the single use of the catalyst (3) having substantially the same composition as the present catalyst system is unable to achieve the effect of the present invention.

EXAMPLE 2

A reaction was carried out in the same manner as in Example 1 except that both the catalyst (1) and the catalyst (2) were molded into rings of 6 mm in outside diameter, 6.6 mm in length and 1 mm in inside diameter of through-hole. The results are shown in Table 1.

COMPARATIVE EXAMPLE 4

A reaction was carried out in the same manner as in Comparative Example 1 except that the catalyst (1) was molded into rings of 6 mm in outside diameter, 6.6 mm in length and 1 mm in inside diameter of through-hole. The results are shown in Table 1.

COMPARATIVE EXAMPLE 5

A reaction was carried out in the same manner as in Comparative Example 2 except that the catalyst (2) was molded into rings of 6 mm in outside diameter, 6.6 mm in length and 1 mm in inside diameter of through-hole. The results are shown in Table 1.

COMPARATIVE EXAMPLE 6

A reaction was carried out in the same manner as in Comparative Example 3 except that the catalyst (3) was molded into rings of 6 mm in outside diameter, 6.6 mm in length and 1 mm in inside diameter of through-hole. The results are shown in Table 1.

In Example 2 and Comparative Examples 4–6, the shapes of the catalysts (1) to (3) were changed from pellets to rings. It is appreciated from the results of Table 1 that the change of catalyst shape to rings gives improvement in yield and reduction in ΔT in all of the catalysts (1) to (3), but the catalyst system of the present invention using the catalysts (1) and (2) in combination gives a higher yield and a lower ΔT than the single use of the catalyst (1), (2) or (3).

EXAMPLE 3

A reaction was carried out in the same manner as in Example 1 except that the reaction was carried out for a long period of time (4,000 hours). The results are shown in Table 1.

It is appreciated from the results of Table 1 that activity reduction is very low even after the reaction 4,000 hours, yield reduction is substantially negligible, and the catalyst system of the present invention enables very stable operation over a long period of time.

COMPARATIVE EXAMPLE 7

A reaction was carried out in the same manner as in Comparative Example 3 except that the reaction time was changed to 4,000 hours. The results are shown in Table 1.

It is appreciated from the results of Table 1 that in Comparative Example 7, as compared with Example 3, activity reduction and yield reduction are both large and the catalyst has a problem in stability.

EXAMPLE 4

A reaction was carried out in the same manner as in Example 2 except that the reaction temperature was changed to 360° C. and the space velocity was changed to 3,000 hr$^{-1}$. The results are shown in Table 1.

COMPARATIVE EXAMPLE 8

A reaction was carried out in the same manner as in Comparative Example 4 except that the reaction temperature was changed to 360° C. and the space velocity was changed to 3,000 hr$^{-1}$. The results are shown in Table 1.

COMPARATIVE EXAMPLE 9

A reaction was carried out in the same manner as in Comparative Example 6 except that the reaction temperature was changed to 360° C. and the space velocity was changed to 3,000 hr$^{-1}$. The results are shown in Table 1.

It is appreciated from the results of Example 4 and Comparative Example 8 and 9 that even when space velocity is increased, the catalyst system of the present invention using the catalysts (1) and (2) in combination shows superiority in activity and yield, over the catalyst (1) or (3).

EXAMPLE 5

A reaction was carried out in the same manner as in Example 2 except that the proportions of isobutylene and nitrogen in material gas were changed to 7% by volume and 69.8% by volume, respectively. The results are shown in Table 1.

COMPARATIVE EXAMPLE 10

A reaction was carried out in the same manner as in Comparative Example 4 except that the proportions of isobutylene and nitrogen in material gas were changed to 7% by volume and 69.8% by volume, respectively. The results are shown in Table 1.

COMPARATIVE EXAMPLE 11

A reaction was carried out in the same manner as in Comparative Example 6 except that the proportions of isobutylene and nitrogen in material gas were changed to 7% by volume and 69.8% by volume, respectively. The results are shown in Table 1.

It is appreciated from the results of Example 5 and Comparative Examples 10 and 11 that even when isobutylene concentration is increased, the catalyst system of the present invention using the catalysts (1) and (2) in combination shows superiority in yield and ΔT over the catalyst (1) or (3). The present catalyst system, as compared with the single use of the catalyst (1) or (3), gives a considerably small increase in ΔT of catalyst layer, in particular. Therefore, it is thought that catalyst arrangement as in the present invention is effective for minimization of catalyst deterioration caused by thermal load.

EXAMPLE 6

A reaction was carried out in the same manner as in Example 1 except that isobutylene was replaced by t-butanol. The results are shown in Table 2.

COMPARATIVE EXAMPLE 12

A reaction was carried out in the same manner as in Comparative Example 1 except that isobutylene was replaced by t-butanol. The results are shown in Table 2.

COMPARATIVE EXAMPLE 13

A reaction was carried out in the same manner as in Comparative Example 3 except that isobutylene was replaced by t-butanol. The results are shown in Table 2.

EXAMPLE 7

A reaction was carried out in the same manner as in Example 2 except that there was used a material gas consisting of 5% by volume of methyl t-butyl ether (MTBE), 13.2% by volume of oxygen, 10% by volume of steam and 71.8% by volume of nitrogen, the reaction temperature was changed to 360° C. and the space velocity was changed to 1,000 hr$^{-1}$. The results are shown in Table 3.

COMPARATIVE EXAMPLE 14

A reaction was carried out in the same manner as in Comparative Example 4 except that there was used a material gas consisting of 5% by volume of MTBE, 13.2% by volume of oxygen, 10% by volume of steam and 71.8% by volume of nitrogen, the reaction temperature was changed to 360° C. and the space velocity was changed to 1,000 hr$^{-1}$. The results are shown in Table 3.

COMPARATIVE EXAMPLE 15

A reaction was carried out in the same manner as in Comparative Example 6 except that there was used a material gas consisting of 5% by volume of MTBE, 13.2% by volume of oxygen, 10% by volume of steam and 71.8% by volume of nitrogen, the reaction temperature was changed to 360° C. and the space velocity was changed to 1,000 hr$^{-1}$. The results are shown in Table 3.

EXAMPLE 8

A catalyst (4) was prepared in the same manner as in Example 1 except that nickel nitrate was used in place of cobalt nitrate, phosphoric acid was added after the addition of ammonium paratungstate, rubidium nitrate was used in place of cesium nitrate, stannic oxide was added after the addition of rubidium nitrate, and aluminum nitrate was used in place of silica sol.

This catalyst (4) had the following composition in terms of atomic ratio excluding oxygen.

$Mo_{12}W_2Bi_3Fe_1Ni_7Rb_1P_{0.2}Sn_{0.5}Al_1$

A catalyst (5) was prepared in the same manner as for the catalyst (4) except that the amount of rubidium nitrate used was changed.

This catalyst (5) had the following composition in terms of atomic ratio excluding oxygen.

$Mo_{12}W_2Bi_3Fe_1Ni_7Rb_{0.2}P_{0.2}Sn_{0.5}Al_1$ 750 ml of the catalyst (4) was filled into the gas inlet portion of a steel-made reaction tube of 25.4 mm in diameter, and 750 ml of the catalyst (5) was filled into the gas outlet portion.

A reaction was carried out in the same manner as in Example 1. The results are shown in Table 4.

COMPARATIVE EXAMPLE 16

A reaction was carried out in the same manner as in Example 8 except that no catalyst (5) was used and only the catalyst (4) (1,500 ml) was filled. The results are shown in Table 4.

COMPARATIVE EXAMPLE 17

A reaction was carried out in the same manner as in Example 8 except that no catalyst (4) was used and only the catalyst (5) (1,500 ml) was filled. The results are shown in Table 4.

EXAMPLE 9

A catalyst (6) was obtained in the same manner as in Example 1 except that no ammonium paratungstate was used, cesium nitrate was replaced by potassium nitrate, lithium nitrate, magnesium nitrate and calcium nitrate, titanium dioxide was used in place of silica sol, and cerous nitrate and niobium pentoxide were used finally. This catalyst (6) had the following composition in terms of atomic ratio excluding oxygen.

$Mo_{12}Bi_1Fe_1Co_{10}K_{1.2}Li_{0.5}Ca_{0.2}Mg_{0.2}Nb_{0.5}Ce_1Ti_1$

A catalyst (7) was prepared in the same manner as for the catalyst (6) except that the amounts of potassium nitrate and lithium nitrate were changed. This catalyst (7) had the following composition in terms of atomic ratio excluding oxygen.

$Mo_{12}Bi_1Fe_1Co_{10}K_{0.5}Li_{0.2}Ca_{0.2}Mg_{0.2}Nb_{0.5}Ce_1Ti_1$ 750 ml of the catalyst (6) was filled into the gas inlet portion of a steel-made reaction tube of 25.4 mm in diameter, and 750 ml of the catalyst (7) was filled into the gas outlet portion.

A reaction was carried out in the same manner as in Example 1. The results are shown in Table 4.

COMPARATIVE EXAMPLE 18

A reaction was carried out in the same manner as in Example 9 except that no catalyst (7) was used and only the catalyst (6) (1,500 ml) was filled. The results are shown in Table 4.

COMPARATIVE EXAMPLE 19

A reaction was carried out in the same manner as in Example 9 except that no catalyst (6) was used and only the catalyst (7) (1,500 ml) was filled. The results are shown in Table 4.

EXAMPLE 10

A suspension was prepared in the same manner as in Example 1 except that no ammonium paratungstate was used, thallous nitrate and strontium nitrate were used in place of cesium nitrate, then there were added tellurium oxide, lead nitrate and zinc nitrate, and titanium dioxide was used in place of silica sol.

The suspension was stirred with heating and subjected to evaporation to dryness. The residue was molded into rings of 6 mm in outside diameter, 6.6 mm in length and 2 mm in inside diameter of through-hole. The rings were fired at 500° C. for 6 hours in an air stream to obtain a catalyst (8). This catalyst (8) had the following composition in terms of atomic ratio excluding oxygen.

$Mo_{12}Bi_1Fe_3Co_7Tl_{0.7}Sr_{0.3}Te_{0.3}Pb_1Zn_{0.5}Ti_1$

A catalyst (9) was obtained in the same manner as for the catalyst (8) except that the amount of thallous nitrate used was changed. This catalyst had the following composition in terms of atomic ration excluding oxygen.

$Mo_{12}Bi_1Fe_3Co_7Tl_{0.05}Sr_{0.3}Te_{0.3}Pb_1Zn_{0.5}Ti_1$ 750 ml of the catalyst (8) was filled into the gas inlet portion of a steel-made reaction tube of 25.4 mm in diameter, and 750 ml of the catalyst (9) was filled into the gas outlet portion.

A reaction was carried out in the same manner as in Example 1. The results are shown in Table 4.

COMPARATIVE EXAMPLE 20

A reaction was carried out in the same manner as in Example 10 except that no catalyst (9) was used and only the catalyst (8) (1,500 ml) was filled. The results are shown in Table 4.

COMPARATIVE EXAMPLE 21

A reaction was carried out in the same manner as in Example 10 except that no catalyst (8) was used and only the catalyst (9) (1,500 ml) was filled. The results are shown in Table 4.

EXAMPLE 11

A suspension was prepared in the same manner as in Example 1 except that cesium nitrate was replaced by potassium nitrate, barium nitrate and beryllium nitrate, then there were added antimony trioxide and manganese nitrate, and silica sol was replaced by zirconium nitrate.

Using this suspension, a catalyst (10) was prepared in the same manner as in Example 10. This catalyst (10) had the following composition in terms of atomic ratio excluding oxygen.

$Mo_{12}W_{1.5}Bi_1Fe_{1.2}Co_5K_{1.8}Ba_{0.2}Be_{0.2}Sb_1Mn_{0.5}Zr_1$

A catalyst (11) was obtained in the same manner as for the catalyst (19) except that potassium nitrate was replaced by sodium nitrate. This catalyst (11) had the following composition in terms of atomic ratio excluding oxygen.

$Mo_{12}W_{1.5}Bi_1Fe_{1.2}Co_5Na_{1.0}Ba_{0.2}Be_{0.2}Sb_1Mn_{0.5}Zr_1$ 750 ml of the catalyst (10) was filled into the gas inlet portion of a steel-made reaction tube of 25.4 mm in diameter, and 750 ml of the catalyst (11) was filled into the gas outlet portion.

A reaction was carried in the same manner as in Example 1. The results are shown in Table 4.

COMPARATIVE EXAMPLE 22

A reaction was carried out in the same manner as in Example 11 except that no catalyst (11) was used and only the catalyst (10) (1,500 ml) was filled. The results are shown in Table 4.

COMPARATIVE EXAMPLE 23

A reaction was carried out in the same manner as in Example 11 except that no catalyst (10) was used and only the catalyst (11) (1,500 ml) was filled. The results are shown in Table 4.

TABLE 1

| | | (Reaction conditions) | | | Selectivity (mole %) | | Total |
|---|---|---|---|---|---|---|---|
| | Method of catalyst filling Inlet portion/Outlet portion | Reaction temperature (°C.) | ΔT (°C.) | Isobutylene conversion (mole %) | Metha- crolein | Methacrylic acid | per-pass yield (mole %) |
| Example 1 | Catalyst (1) pellets/catalyst (2) pellets | 340 | 70 | 99.0 | 85.6 | 3.6 | 88.3 |
| Comparative Example | | | | | | | |
| 1 | Single layer of catalyst (1) pellets | 340 | 70 | 95.9 | 85.8 | 3.2 | 85.4 |
| 2 | Single layer of catalyst (2) pellets | 340 | 92 | 99.5 | 79.5 | 5.4 | 84.5 |
| 3 | Single layer of catalyst (3) pellets | 340 | 85 | 98.3 | 84.3 | 3.6 | 86.4 |
| Example 2 | Catalyst (1) rings/catalyst (2) rings | 340 | 61 | 99.5 | 86.9 | 3.1 | 89.6 |
| Comparative Example | | | | | | | |
| 4 | Single layer of catalyst (1) rings | 340 | 62 | 96.1 | 86.9 | 3.0 | 86.4 |
| 5 | Single layer of catalyst (2) rings | 340 | 84 | 99.6 | 81.5 | 5.0 | 86.2 |
| 6 | Single layer of catalyst (3) rings | 340 | 76 | 99.0 | 85.5 | 3.3 | 87.9 |
| Example 3 | Catalyst (1) pellets/catalyst (2) pellets | 340 | 52 | 98.5 | 86.5 | 3.1 | 88.3 |
| Comparative Example 7 | Single layer of catalyst (3) pellets | 340 | 65 | 95.1 | 84.7 | 3.4 | 83.8 |
| Example 4 | Catalyst (1) rings/catalyst (2) rings | 360 | 63 | 99.0 | 86.7 | 3.0 | 88.8 |
| Comparative Example | | | | | | | |
| 8 | Single layer of catalyst (1) rings | 360 | 65 | 94.8 | 86.3 | 3.0 | 84.7 |
| 9 | Single layer of catalyst (3) rings | 360 | 80 | 97.7 | 84.9 | 3.4 | 86.3 |
| Example 5 | Catalyst (1) rings/catalyst (2) rings | 340 | 66 | 99.7 | 86.2 | 3.3 | 89.3 |
| Comparative Example | | | | | | | |
| 10 | Single layer of catalyst (1) rings | 340 | 66 | 96.4 | 85.0 | 3.4 | 85.2 |
| 11 | Single layer of catalyst (3) rings | 340 | 81 | 99.3 | 83.9 | 3.5 | 86.8 |

Notes:
Example 3, Comparative Example 7 = after 4,000 hours of continuous operation
Example 4, Comparative Examples 8 and 9 = space velocity 1,600→3,000 hr$^{-1}$
Example 5, Comparative Examples 10 and 11 = isobutylene concentration 6→7% by volume

TABLE 2

| | | (Reaction conditions) | | | Per-pass yield (mole %) | | Total |
|---|---|---|---|---|---|---|---|
| | Method of catalyst filling Inlet portion/Outlet portion | Reaction temperature (°C.) | ΔT (°C.) | t-Butanol conversion (mole %) | Metha- crolein | Methacrylic acid | per-pass yield (mole %) |
| Example 6 | Catalyst (1) pellets/catalyst (2) pellets | 340 | 61 | 100.0 | 85.2 | 3.3 | 88.5 |
| Comparative Example | | | | | | | |
| 12 | Single layer of catalyst (1) pellets | 340 | 61 | 100.0 | 82.8 | 2.9 | 85.7 |
| 13 | Single layer of catalyst (3) pellets | 340 | 75 | 100.0 | 83.6 | 3.2 | 86.8 |

TABLE 3

| | | (Reaction conditions) | | | Selectivity (mole %) | | Total |
|---|---|---|---|---|---|---|---|
| | Method of catalyst filling Inlet portion/Outlet portion | Reaction temperature (°C.) | ΔT (°C.) | MTBE conversion (mole %) | Metha- crolein | Metha- crylic acid | per-pass yield (mole %) |
| Example 7 | Catalyst (1) rings/catalyst (2) rings | 360 | 61 | 98.3 | 82.5 | 4.3 | 85.6 |
| Comparative Example | | | | | | | |
| 14 | Single layer of catalyst (1) rings | 360 | 61 | 95.1 | 82.7 | 4.5 | 82.9 |
| 15 | Single layer of catalyst (3) rings | 360 | 76 | 97.8 | 81.2 | 4.6 | 83.9 |

TABLE 4

| | Method of catalyst filling Inlet portion/Outlet portion | Reaction temperature (°C) | ΔT (°C) | Isobutylene conversion (mole %) | Selectivity (mole %) Methacrolein | Selectivity (mole %) Methacrylic acid | Total per-pass yield (mole %) |
|---|---|---|---|---|---|---|---|
| Example 8 | Catalyst (4) pellets/catalyst (5) pellets | 340 | 66 | 98.5 | 84.9 | 3.3 | 86.9 |
| Comparative Example | | | | | | | |
| 16 | Single layer of catalyst (4) pellets | 340 | 66 | 94.6 | 85.1 | 3.0 | 83.3 |
| 17 | Single layer of catalyst (5) pellets | 340 | 90 | 99.0 | 78.2 | 5.1 | 82.5 |
| Example 9 | Catalyst (6) pellets/catalyst (7) pellets | 340 | 65 | 96.8 | 83.4 | 3.1 | 83.7 |
| Comparative Example | | | | | | | |
| 18 | Single layer of catalyst (6) pellets | 340 | 65 | 92.5 | 83.7 | 2.7 | 79.9 |
| 19 | Single layer of catalyst (7) pellets | 340 | 91 | 97.5 | 77.1 | 4.8 | 79.9 |
| Example 10 | Catalyst (8) rings/catalyst (9) rings | 340 | 60 | 97.5 | 86.2 | 3.0 | 87.0 |
| Comparative Example | | | | | | | |
| 20 | Single layer of catalyst (8) rings | 340 | 60 | 94.1 | 86.3 | 2.8 | 83.8 |
| 21 | Single layer of catalyst (9) rings | 340 | 81 | 97.8 | 80.6 | 4.9 | 83.6 |
| Example 11 | Catalyst (10) rings/catalyst (11) rings | 340 | 59 | 98.6 | 84.3 | 2.9 | 86.0 |
| Comparative Example | | | | | | | |
| 22 | Single layer of catalyst (10) rings | 340 | 58 | 93.9 | 84.7 | 2.6 | 82.2 |
| 23 | Single layer of catalyst (11) rings | 340 | 79 | 99.1 | 78.2 | 4.2 | 81.7 |

EXAMPLE 1-a 1,456 g of cobalt nitrate and 202 g of ferric nitrate were dissolved in 1,000 ml of water. 243 g of bismuth nitrate was dissolved in an aqueous nitric acid solution consisting of 30 ml of concentrated nitric acid and 120 ml of water.

Separately, 1,059 g of ammonium paramolybdate and 265 g of ammonium paratungstate were dissolved in 3,000 ml of water being stirred with heating. To the resulting aqueous solution were dropwise added the above prepared two aqueous solutions, and mixing was carried out. Thereto were added an aqueous solution obtained by dissolving 68.3 g of cesium nitrate in 200 ml of water, and 203 g of silica sol of 20 weight % concentration in this order, and mixing was carried out.

The thus obtained suspension was stirred with heating, and subjected to evaporation to dryness. The residue was molded into pellets of 6 mm in outside diameter and 6.6 mm in length. The pellets were fired at 510° C. for 6 hours in an air stream to obtain a catalyst (1-a). This catalyst (1-a) had the following composition in terms of atomic ratio excluding oxygen.

$$Mo_{12}W_2Bi_1Fe_1Co_{10}Cs_{0.7}Si_{1.35}$$

A catalyst (2-a) was prepared in the same manner as in the preparation of the catalyst (1-a) except that the amount of cesium nitrate was changed to 9.8 g and the firing temperature was changed to 480° C.

This catalyst (2-a) had the following composition in terms of atomic ratio excluding oxygen.

$$Mo_{12}W_2Bi_1Fe_1Co_{10}Cs_{0.1}Si_{1.35}$$

With respect to the activities of the catalysts (1-a) and (2-a), the catalyst (2-a) has a higher activity than the catalyst (1-a), as is clear from the results of Comparative Examples 1-a and 2-a shown later.

750 ml of the catalyst (1-a) was filled into the material gas inlet portion of a steel-made reaction tube of 25.4 mm in diameter, and 750 ml of the catalyst (2-a) was filled into the material gas outlet portion.

A mixed gas of a composition consisting of 6% by volume of isobutylene, 13.2% by volume of oxygen, 10% by volume of steam and 70.8% by volume of nitrogen was introduced from the inlet of the reaction tube, and a reaction was carried out at a reaction temperature of 340° C. at a space velocity (SV) of 1,600 hr$^{-1}$ (STP). The results are shown in Table 1-a.

COMPARATIVE EXAMPLE 1-a

A reaction was carried out in the same manner as in Example 1-a except that no catalyst (2-a) was used and only the catalyst (1-a) (1,500 ml) was filled. The results are shown in Table 1-a.

COMPARATIVE EXAMPLE 2-a

A reaction was carried out in the same manner as in Example 1-a except that no catalyst (1-a) was used and only the catalyst (2-a) (1,500 ml) was filled. The results are shown in Table 1-a.

COMPARATIVE EXAMPLE 3-a

A catalyst (3-a) was prepared in the same manner as for the catalyst (1-a) of Example 1-a except that the amount of cesium nitrate was changed to 39 g.

This catalyst (3-a) had the following composition in terms of atomic ratio excluding oxygen.

$$Mo_{12}W_2Bi_1Fe_1Co_{10}Cs_{0.4}Si_{1.35}$$

A reaction was carried out in the same manner as in Example 1-a except that only the catalyst (3-a) (1,500 ml) was filled into the reaction tube. The results are shown in Table 1-a.

COMPARATIVE EXAMPLE 4-1

A catalyst (4-a) and a catalyst (5-a) were prepared in the same manners as for the catalyst (1-a) and the catalyst (2-a), respectively, except that the firing temperatures used in the preparations of the catalyst (1-a) and the catalyst (2-a) were both changed to 500° C. 750 ml of the catalyst (4-a) was filled into the reaction gas inlet portion, and 750 ml of the catalyst (5-a) was filled into the outlet portion. Then, a reaction was carried out in the same manner as in Example 1-a. The results are shown in Table 1-a.

It is appreciated from the results of Example 1-a and Comparative Examples 1-a to 3-a that the catalyst (1-a) has a very low activity, the catalyst (2-a) has a high activity, and both of them give a low total per-pass yield while the catalyst system of the present invention which is a combination of the catalysts (1-a) and (2-a), gives high total per-pass yield and produces intended methacrolein and methacrylic acid at high yields.

When the catalyst (3-a) having a composition intermediate between those of the catalysts (1-a) and (2-a) is compared with the catalyst system of the present invention which is a combination of the catalysts (1-a) and (2-a), the catalyst (3-a) gives a low total per-pass yield and a very large temperature difference (a very large $\Delta T$) between the reaction temperature and the hot spots temperature. Therefore, it is thought that catalyst deterioration due to thermal load is striking in the catalyst (3-a). Accordingly, it is appreciated that the single use of the catalyst (3-a) having substantially the same composition as the present catalyst system in unable to achieve the effect of the present invention.

Further, it is clear that Comparative Example 4-a is superior to Comparative Examples 1-a to 3-a in yield and $\Delta T$ but, inferior to Example 1-a using the catalysts of the present invention in said properties. Thus, it is appreciated that the variation of the firing temperature in addition to the variation of the B group elements gives a further improved element.

EXAMPLE 2-a

A reaction was carried out in the same manner as in Example 1-a except that the catalysts (1-a) and (2-a) were both molded into rings of 6 mm in outside diameter, 6.6 mm in length and 1 mm in inside diameter of through-hole. The results are shown in Table 1-a.

COMPARATIVE EXAMPLE 5-a

A reaction was carried out in the same manner as in Comparative Example 1-a except that the catalyst (1-a) was molded into rings of 6 mm in outside diameter, 6.6 mm in length and 1 mm in inside diameter of through-hole. The results are shown in Table 1-a.

COMPARATIVE EXAMPLE 6-a

A reaction was carried out in the same manner as in Comparative Example 2-a except that the catalyst (2-a) was molded into rings of 6 mm in outside diameter, 6.6 mm in length and 1 mm in inside diameter of through-hole. The results are shown in Table 1-a.

COMPARATIVE EXAMPLE 7-a

A reaction was carried out in the same manner as in Comparative Example 3-a except that the catalyst (3-a) was molded into rings of 6 mm in outside diameter, 6.6 mm in length and 1 mm in inside diameter of through-hole. The results are shown in Table 1-a.

COMPARATIVE EXAMPLE 8-a

A reaction was carried out in the same manner as in Comparative Example 4-a except that the catalysts (4-a) and (5-a) were both molded into rings of 6 mm in outside diameter, 6.6 mm in length and 1 mm in inside diameter of through-hole. The results are shown in Table 1-a.

In Examples 2-a and Comparative Examples 5-a to 8-a, the shapes of the catalysts (1-a) to (5-a) were changed from pellets to rings. It is appreciated from the results of Table 1-a that the variation of the catalyst shape into rings gives an improvement in yield and a reduction in $\Delta T$ in each case of the catalysts (1-a) to (3-a) and the combined use of the catalysts (4-a) and (5-a), but the catalyst system of the present invention using the catalysts (1-a) and (2-a) in combination gives an even better yield and an even better $\Delta T$.

EXAMPLES 3-a

A reaction was carried out in the same manner as in Example 1-a except that the reaction was carried out for a longer period up to 4,000 hours. The results are shown in Table 1-a.

It is appreciated from the results of Table 1-a that even after the reaction of 4,000 hours, the reduction in catalyst activity is very low and the reduction in yield is substantially negligible and that the catalyst system of the present invention enables very stable continuous operation over a long period of time.

COMPARATIVE EXAMPLE 9-a

A reaction was carried out in the same manner as in Comparative Example 3-a except that the reaction was carried out for a longer period up to 4,000 hours. The results are shown in Table 1-a.

In each case of Example 3-a and Comparative Example 9-a, the reductions in catalyst activity and yield after 4,000 hours are very small, and there is no large difference in catalyst stability between Example 3-a and Comparative Example 9-a. It is clear therefore that the superiority in yield, of Example 1-a of the present invention over Comparative Example 4-a appears even after 4,000 hours.

EXAMPLE 4-a

A reaction was carried out in the same manner as in Example 2-a except that the reaction temperature was changed to 360° C. and the space velocity was changed to 3,000 hour$^{-1}$ (STP). The results are shown in Table 1-a.

COMPARATIVE EXAMPLE 10-a

A reaction was carried out in the same manner as in Comparative Example 4-a except that the reaction temperature was changed to 360° C. and the space velocity was changed to 3,000 hour$^{-1}$ (STP) The results are shown in Table 1-a.

It is appreciated from the results of Example 4-a and Comparative Example 10-a that the superiority in activity and yield, of the catalyst system of the present invention using the catalysts (1-a) and (2-a) in combination, over the catalyst system using the catalysts (4-a) and (5-a) in combination appears even when the space velocity is increased.

EXAMPLE 5-a

A reaction was effected in the same manner as in Example 2-a except that the proportions of isobutylene and nitrogen in material gas were changed to 7% by volume and 69.8% by volume, respectively. The results are shown in Table 1-a.

COMPARATIVE EXAMPLE 11-a

A reaction was effected in the same manner as in Comparative Example 4-a except that the proportions of isobutylene and nitrogen in material gas were changed to 7% by volume and 69.8% by volume, respectively. The results are shown in Table 1-a.

It is appreciated from the results of Example 5-a and Comparative Example 11-a that the superiority in yield and $\Delta T$, of the catalyst system of the present invention using the catalysts (1-a) and (2-a) in combination, over the catalyst system using the catalysts (4-a) and (5-a) in combination appears even when the isobutylene concentration is incerased.

EXAMPLE 6-a

A reaction was carried out in the same manner as in Example 1-a except that t-butanol was used in place of isobutylene. The results are shown in Table 2-a.

COMPARATIVE EXAMPLE 12-a

A reaction was carried out in the same manner as in Comparative Example 4-a except that t-butanol was used in place of isobutylene. The results are shown in Table 2-a.

EXAMPLE 7-a

A reaction was carried out in the same manner as in Example 2-a except that there was used, as the material gas, a mixed gas consisting of 5% by volume of methyl t-butyl ether (MTBE), 13.2% by volume of oxygen, 10% by volume of steam and 71.8% by volume of nitrogen, the reaction temperature was changed to 360° C. and the space velocity was changed to 1,000 hr$^{-1}$ (STP). The results are shown in Table 3-a.

COMPARATIVE EXAMPLE 13-a

A reaction was carried out in the same manner as in Comparative Example 4-a except that there was used, as the material gas, a mixed gas consisting of 5% by volume of methyl t-butyl ether (MTBE), 13.2% by volume of oxygen, 10% by volume of steam and 71.8% by volume of nitrogen, the reaction temperature was changed to 360° C. and the space velocity was changed to 1,000 hr$^{-1}$ (STP). The results are shown in Table 3 a.

EXAMPLE 8-a

A catalyst (6-a) was prepared in the same manner as in Example 1-a except that nickel nitrate was used in place of cobalt nitrate, phosphoric acid was added after ammonium paratungstate, rubidium nitrate was used in place of cesium nitrate, stannic oxide was added after rubidium nitrate, aluminum nitrate was used in place of silica sol, and the firing temperature was changed to 520° C.

This catalyst (6-a) had the following composition in terms of atomic ratio excluding oxygen.

$Mo_{12}W_2Bi_3Fe_1Ni_7Rb_1P_{0.2}Sn_{0.5}Al_1$

A catalyst (7-a) was prepared in the same manner as for the catalyst (6-a) except that the amount of rubidium nitrate used was changed and the firing temperature was changed to 490° C.

This catalyst (7-a) had the following composition in terms of atomic ratio excluding oxygen.

$Mo_{12}W_2Bi_3Fe_1Ni_7Rb_{0.2}P_{0.2}Sn_{0.5}Al_1$ 750 ml of the catalyst (6-a) was filled into the gas inlet portion of a steel-made reaction tube of 25.4 mm in diameter, and 750 ml of the catalyst (7-a) was filled into the gas outlet portion.

A reaction was carried out in the same manner as in Example 1-a. The results are shown in Table 4-a.

COMPARATIVE EXAMPLE 14-a

A catalyst (8-a) and a catalyst (9-a) were prepared in the same manner as for the catalyst (6-a) and the catalyst (7-a), respectively, except that the firing temperature was changed to 500° C. in each preparation. 750 ml of the catalyst (8-a) was filled into the reaction gas inlet portion, and 750 ml of the catalyst (9-a) was filled into the reaction gas outlet portion. A reaction was carried out in the same manner as in Example 8-a. The results are shown in Table 4-a.

EXAMPLE 9-a

A catalyst (10-a) was obtained in the same manner as in Example 1-a except that no ammonium paratungstate was used, cerium nitrate was replaced by potassium nitrate, lithium nitrate, magnesium nitrate and calcium nitrate, titanium dioxide was used in place of silica sol, finally there were used cerous nitrate and niobium pentoxide, and the firing temperature was changed to 520° C.

This catalyst (10-a) had the following composition in terms of atomic ratio excluding oxygen.

$Mo_{12}Bi_1Fe_1Co_{10}K_{1.2}Li_{0.5}Ca_{0.2}Mg_{0.2}Nb_{0.5}Ce_1Ti_1$

A catalyst (11-a) was prepared in the same manner as for the catalyst (10-a) except that the amounts of potassium nitrate and lithium nitrate used were changed and the firing temperature was changed to 480° C.

This catalyst (11-a) has the following composition in terms of atomic ratio excluding oxygen.

$Mo_{12}Bi_1Fe_1CO_{10}K_{0.5}Li_{0.2}Ca_{0.2}Mg_{0.2}Nb_{0.5}Ce_1Ti_1$ 750 ml of the catalyst (10-a) was filled into the gas inlet portion of a steel-made reaction tube of 25.4 mm in diameter, and 750 ml of the catalyst (11-a) was filled into the gas outlet portion.

A reaction was carried out in the same manner as in Example 1-a. The results are shown in Table 4-a.

COMPARATIVE EXAMPLE 15-a

A catalyst (12-a) and a catalyst (13-a) were prepared in the same manners as for the catalyst (10-a) and the catalyst (11-a), respectively, except that the firing temperature was 500° C. in each preparation. 750 ml of the catalyst (12-a) was filled into the reaction gas inlet portion, and 750 ml of the catalyst (13-a) was filled into the reaction gas outlet portion. A reaction was carried out in the same manner as in Example 9-a. The results are shown in Table 4-a.

EXAMPLE 10-a

A suspension was prepared in the same manner as in Example 1-a except that no ammonium paratungstate was used, thallous nitrate and strontium nitrate were used in place of cesium nitrate, thereafter there were added tellurium oxide, lead nitrate and zinc nitrate, silica sol replaced by titanium dioxide, and the firing temperature was changed to 530° C.

The suspension was stirred with heating and subjected evaporation to dryness. The residue was molded into rings of 6 mm in outside diameter, 6.6 mm in length and 2 mm in inside diameter of through-hole, and fired at 500° C. for 6 hours in an air stream to obtain a catalyst (14-a).

The catalyst (14-a) had the following composition in terms of atomic ratio excluding oxygen.

$Mo_{12}Bi_1Fe_3Co_7Tl_{0.7}Sr_{0.3}Te_{0.3}Pb_1Zn_{0.5}Ti_1$

A catalyst (15-a) was prepared in the same manner as for the catalyst (14-a) except that the amount of thallous nitrate was changed and the firing temperature was changed to 480° C.

The catalyst (15-a) had the following composition in terms of atomic ratio excluding oxygen.

$$Mo_{12}Bi_1Fe_3Co_7Tl_{0.05}Sr_{0.3}Te_{0.3}Pb_1Zn_{0.5}Ti_1$$

750 ml of the catalyst (14-a) was filled into the gas inlet portion of a steel-made reactor of 25.4 mm in diameter, and 750 ml of the catalyst (15-a) was filled into the gas outlet portion.

A reaction was carried out in the same manner as in Example 1-a. The results are shown in Table 4-a.

COMPARATIVE EXAMPLE 16-a

A catalyst (16-a) and a catalyst (17-a) were prepared in the same manners as for the catalyst (14-a) and the catalyst (15-a), respectively, except that the firing temperatures used in Example 10-a for the preparation of the catalyst (14-a) and the catalyst (15-a) were changed to 500° C. 750 ml of the catalyst (16-a) was filled into the reaction gas inlet portion, and 750 ml of the catalyst (17-a) was filled into the reaction gas outlet portion. A reaction was carried out in the same manner as in Example 10-a. The results are shown in Table 4-a.

EXAMPLE 11-a

A suspension was prepared in the same manner as in Example 1-a except that cesium nitrate was replaced by potassium nitrate, barium nitrate and beryllium nitrate, then antimony trioxide and manganese nitrate were added, silica sol was replaced by zirconium nitrate, and the firing temperature was changed to 530° C.

Using this suspension, the procedure of Example 10-a was repeated to prepare a catalyst (18-a).

The catalyst (18-a) had the following composition in terms of atomic ratio excluding oxygen.

$$Mo_{12}W_{1.5}Bi_1Fe_{1.2}Co_5K_{1.8}Ba_{0.2}Be_{0.2}Sb_1Mn_{0.5}Zr_1$$

A catalyst (19-a) was obtained in the same manner as for the catalyst (18-a) except that potassium nitrate was replaced by sodium nitrate and the firing temperature was changed to 470° C.

The catalyst (19-a) had the following composition in terms of atomic ratio excluding oxygen.

$$Mo_{12}W_{1.5}Bi_1Fe_{1.2}Co_{0.5}Na_{1.0}Ba_{0.2}Be_{0.2}Sb_1Mn_{0.5}Zr_1$$

750 ml of the catalyst (18-a) was filled into the gas inlet portion of a steel-made reaction tube of 25.4 mm in diameter, and 750 ml of the catalyst (19-a) was filled into the gas outlet portion.

A reaction was carried out in the same manner as in Example 1-a. The results are shown in Table 4-a.

COMPARATIVE EXAMPLE 17-a

A catalyst (20-a) and a catalyst (21-a) were prepared in the same manners as for the catalyst (18-a) and the catalyst (19-a), respectively, except that the firing temperatures used in Example 11-a for the preparation of the catalyst (18-a) and the catalyst (19-a) were changed to 500° C. 750 ml of the catalyst (20-a) was filled into the reaction gas inlet portion, and 750 ml of the catalyst (21-a) was filled into the gas outlet portion. A reaction was carried out in the same manner as in Example 11-a. The results are shown in Table 4-a.

TABLE 1-a

| | Method of catalyst filling Inlet portion/Outlet portion | Reaction temperature (°C.) | ΔT (°C.) | Isobutylene conversion (mole %) | Selectivity (mole %) Methacrolein | Selectivity (mole %) Methacrylic acid | Total per-pass yield (mole %) |
|---|---|---|---|---|---|---|---|
| Example 1-a | Catalyst (1-a) Pellets/catalyst (2-a) pellets | 340 | 68 | 99.1 | 86.6 | 3.4 | 89.2 |
| Comparative Example | | | | | | | |
| 1-a | Single layer of catalyst (1-a) pellets | 340 | 68 | 95.2 | 86.5 | 3.4 | 85.6 |
| 2-a | Single layer of catalyst (2-a) pellets | 340 | 93 | 99.6 | 79.0 | 5.6 | 84.3 |
| 3-a | Single layer of catalyst (3-a) pellets | 340 | 84 | 97.8 | 84.5 | 3.3 | 85.9 |
| 4-a | Catalyst (4-a) pellets/catalyst (5-a) pellets | 340 | 70 | 99.0 | 85.6 | 3.6 | 88.3 |
| Example 2-a | Catalyst (1-a) rings/catalyst (2-a) rings | 340 | 60 | 99.5 | 88.0 | 3.0 | 90.5 |
| Comparative Example | | | | | | | |
| 5-a | Single layer of catalyst (1-a) rings | 340 | 61 | 95.5 | 87.9 | 2.9 | 86.7 |
| 6-a | Single layer of catalyst (2-a) rings | 340 | 85 | 99.7 | 80.9 | 5.3 | 85.9 |
| 7-a | Single layer of catalyst (3-a) rings | 340 | 74 | 98.4 | 85.6 | 3.1 | 87.3 |
| 8-a | Catalyst (4-a) rings/catalyst (5-a) rings | 340 | 61 | 99.5 | 86.9 | 3.1 | 89.6 |
| Example 3-a | Catalyst (1-a) rings/catalyst (2-a) pellets | 340 | 49 | 98.4 | 87.6 | 2.9 | 89.1 |
| Comparative Example 9-a | Catalyst (4-a) pellets/catalyst (5-a) pellets | 340 | 52 | 98.5 | 86.5 | 3.1 | 88.3 |
| Example 4-a | Catalyst (1-a) rings/catalyst (2-a) rings | 360 | 62 | 98.8 | 87.9 | 2.8 | 89.6 |
| Comparative Example 10-a | Catalyst (4-a) rings/catalyst (5-a) rings | 360 | 63 | 99.0 | 86.7 | 3.0 | 88.8 |
| Example 5-a | Catalyst (1-a) rings/catalyst (2-a) rings | 340 | 64 | 99.5 | 87.2 | 3.2 | 89.9 |
| Comparative 11-a | Catalyst (4-a) rings/catalyst (5-a) rings | 340 | 66 | 99.7 | 86.2 | 3.3 | 89.3 |

Notes:
Example 3-a, Comparative Example 9-a = after 4,000 hours of continuous operation
Example 4-a, Comparative Examples 10-a = space velocity 1,600→3,000 hr$^{-1}$ (STP)
Example 5-a, Comparative Examples 11-a = isobutylene concentration 6→7% by volume

TABLE 2-a

| | Method of catalyst filling Inlet portion/Outlet portion | Reaction temperature (°C.) | ΔT (°C.) | t-Butanol conversion (mole %) | Per-pass yield (mole %) Methacrolein | Per-pass yield (mole %) Methacrylic acid | Total per-pass yield (mole %) |
|---|---|---|---|---|---|---|---|
| Example 6-a | Catalyst (1-a) pellets/catalyst (2-a) pellets | 340 | 59 | 100.0 | 86.1 | 3.1 | 89.2 |

TABLE 2-a-continued

| | Method of catalyst filling Inlet portion/Outlet portion | (Reaction conditions) Reaction temperature (°C.) | ΔT (°C.) | t-Butanol conversion (mole %) | Per-pass yield (mole %) Methacrolein | Methacrylic acid | Total per-pass yield (mole %) |
|---|---|---|---|---|---|---|---|
| Comparative Example 12-a | Catalyst (4-a) pellets/catalyst (5-a) pellets | 340 | 61 | 100.0 | 85.2 | 3.3 | 88.5 |

TABLE 3-a

| | Method of catalyst filling Inlet portion/Outlet portion | (Reaction conditions) Reaction temperature (°C.) | ΔT (°C.) | MTBE conversion (mole %) | Selectivity (mole %) Methacrolein | Methacrylic acid | Total per-pass yield (mole %) |
|---|---|---|---|---|---|---|---|
| Example 7-a | Catalyst (1-a) pellets/catalyst (2-a) pellets | 360 | 60 | 98.1 | 83.6 | 4.2 | 86.1 |
| Comparative Example 13-a | Catalyst (4-a) pellets/catalyst (5-a) pellets | 360 | 61 | 98.3 | 82.5 | 4.3 | 85.3 |

TABLE 4-a

| | Method of catalyst filling Inlet portion/Outlet portion | (Reaction conditions) Reaction temperature (°C.) | ΔT (°C.) | Isobutylene conversion (mole %) | Selectivity (mole %) Methacrolein | Methacrylic acid | Total per-pass yield (mole %) |
|---|---|---|---|---|---|---|---|
| Example 8-a | Catalyst (6-a) Pellets/catalyst (7-a) pellets | 340 | 65 | 98.4 | 85.9 | 3.3 | 87.8 |
| Comparative Example 14-a | Catalyst (8-a) pellets/catalyst (9-a) pellets | 340 | 66 | 98.5 | 84.9 | 3.3 | 86.9 |
| Example 9-a | Catalyst (10-a) pellets/catalyst (11-a) pellets | 340 | 64 | 96.5 | 84.6 | 3.0 | 84.5 |
| Comparative Example 15-a | Catalyst (12-a) pellets/catalyst (13-a) pellets | 340 | 65 | 96.8 | 83.4 | 3.1 | 83.7 |
| Example 10-a | Catalyst (14-1) pellets/catalyst (15-a) pellets | 340 | 58 | 97.2 | 87.5 | 2.8 | 87.8 |
| Comparative Example 16-a | Catalyst (16-a) rings/catalyst (17-a) rings | 340 | 60 | 97.5 | 86.2 | 3.0 | 87.0 |
| Example 11-a | Catalyst (18-a) rings/catalyst (19-a) rings | 340 | 58 | 98.4 | 85.4 | 2.8 | 86.8 |
| Comparative Example 17-a | Catalyst (20-a) rings/catalyst (21-a) rings | 340 | 59 | 98.6 | 84.3 | 2.9 | 86.0 |

EXAMPLE 1-b 1,456 g of cobalt nitrate and 202 g of ferric nitrate were dissolved in 1,000 ml of water. 243 g of bismuth nitrate was dissolved in an aqueous nitric acid solution consisting of 30 ml of concentrated nitric acid and 120 ml of water.

Separately, 1,059 g of ammonium paramolybdate and 265 g of ammonium paratungstate were dissolved in 3,000 ml of water being stirred with heating. To the resulting aqueous solution were dropwise added the above prepared two aqueous solutions, and mixing was carried out. Thereto were added an aqueous solution obtained by dissolving 68.3 g of cesium nitrate and 13.1 g of barium nitrate in 400 ml of water, and 203 g of silica sol of 20 weight % concentration in this order, and mixing was carried out.

The thus obtained suspension was stirred with heating, and subjected to evaporation to dryness. The residue was molded into pellets of 6 mm in outside diameter and 6.6 mm in length. The pellets were fired at 500° C. for 6 hours in an air stream to obtain a catalyst (1-b). This catalyst (1-b) had the following composition in terms of atomic ratio excluding oxygen.

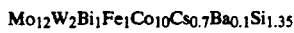

$Mo_{12}W_2Bi_1Fe_1Co_{10}Cs_{0.7}Ba_{0.1}Si_{1.35}$

A catalyst (2-b) was prepared in the same manner as in the preparation of the catalyst (1-b) except that the amount of barium nitrate was changed to 65.3 g. This catalyst (2-b) had the following composition in terms of atomic ratio excluding oxygen.

$Mo_{12}W_2Bi_1Fe_1Co_{10}Cs_{0.7}Ba_{0.6}Si_{1.35}$

With respect to the activities of the catalysts (1-b) and (2-b), the catalyst (2-b) has a higher activity than the catalyst (1-b), as is clear from the results of Comparative Examples 1-b and 2-b shown later.

750 ml of the catalyst (1-b) was filled into the material gas inlet portion of a steel-made reaction tube of 25.4 mm in diameter, and 750 ml of the catalyst (2-b) was filled into the material gas outlet portion.

A mixed gas of a composition consisting of 6% by volume of isobutylene, 13.2% by volume of oxygen, 10% by volume of steam and 70.8% by volume of nitrogen was introduced from the inlet of the reaction tube, and a reaction was carried out at a reaction temperature of 340° C. at a space velocity (SV) of 1,600 hu$^{-1}$ (STP). The results are shown in Table 1-b.

COMPARATIVE EXAMPLE 1-b

A reaction was carried out in the same manner as in Example 1-b except that no catalyst (2-b) was used and only the catalyst (1-b) (1,500 ml) was filled. The results are shown in Table 1-b.

COMPARATIVE EXAMPLE 2-b

A reaction was carried out in the same manner as in Example 1-b except that no catalyst (1-b) was used and only the catalyst (2-b) (1,500 ml) was filled. The results are shown in Table 1-b.

COMPARATIVE EXAMPLE 3-b

A catalyst (3-b) was prepared in the same manner as for the catalyst (1-b) of Example 1-b except that the amount of barium nitrate was changed to 39.2 g. This catalyst (3-b) had the following composition in terms of atomic ratio excluding oxygen.

$Mo_{12}W_2Bi_1Fe_1Co_{10}Cs_{0.7}Ba_{0.35}Si_{1.35}$

A reaction was carried out in the same manner as in Example 1-b except that only the catalyst (3-b) (1,500 ml) was filled into the reaction tube. The results are shown in Table 1-b.

It is appreciated from the results of Table 1-b that the catalyst (1-b) has a very low activity, the catalyst (2-b) has a high activity but a low selectivity, and both of them give a low total per-pass yield while the catalyst system of the present invention which is a combination of the catalysts (1-b) and (2-b), gives a high total per-pass yield and produces intended methacrolein and methacrylic acid at high yields.

When the catalyst (3-b) having a composition intermediate between those of the catalysts (1-b) and (2-b) is compared with the catalyst system of the present invention which is a combination of the catalysts (1-b) and (2-b), the catalyst (3-b) gives a low total per-pass yield and a very large temperature difference (a very large $\Delta T$) between the reaction temperature and the highest temperature in catalyst layer. Therefore, it is thought that catalyst deterioration due to thermal load is striking in the catalyst (3-b). Accordingly, it is appreciated that the single use of the catalyst (3-b) having substantially the same composition as the present catalyst system is unable to achieve the effect of the present invention.

EXAMPLE 2-b

A reaction was carried out in the same manner as in Example 1-b except that the catalysts (1-b) and (2-b) were both molded into rings of 6 mm in outside diameter, 6.6 mm in length and 1 mm in inside diameter of through-hole. The results are shown in Table 1-b.

COMPARATIVE EXAMPLE 4-b

A reaction was carried out in the same manner as in Comparative Example 1-b except that the catalyst (1-b) was molded into rings of 6 mm in outside diameter, 6.6 mm in length and 1 mm in inside diameter of through-hole. The results are shown in Table 1-b.

COMPARATIVE EXAMPLE 1-b

A reaction was carried out in the same manner as in Comparative Example 2-b except that the catalyst (2-b) was molded into rings of 6 mm in outside diameter, 6.6 mm in length and 1 mm in inside diameter of through-hole. The results are shown in Table 1-b.

COMPARATIVE EXAMPLE 6-b

A reaction was carried out in the same manner as in Comparative Example 3-b except that the catalyst (3-b) was molded into rings of 6 mm in outside diameter, 6.6 mm in length and 1 mm in inside diameter of through-hole. The results are shown in Table 1-b.

In Example 2-b and Comparative Examples 4-b to 6-b, the shapes of the catalysts (1-b) to (3-b) were changed from pellets to rings. It is appreciated from the results of Table 1-b that the change of catalyst shape to rings gives improvement in yield and reduction in $\Delta T$ in all of the catalysts (1-b) to (3-b), but the catalyst system of the present invention using the catalysts (1-b) and (2-b) in combination gives a higher yield and a lower $\Delta T$ than the single use of the catalyst (1-b), (2-b) or (3-b).

EXAMPLE 3-b

A reaction was carried out in the same manner as in Example 1-b except that the reaction was carried out for an extended period of time up to 4,000 hours. The results are shown in Table 1-b.

It is appreciated from the results of Table 1-b that activity reduction is very low even after the reaction of 4,000 hours, yield reduction is substantially negligible, and the catalyst system of the present invention enables very stable operation over a long period of time.

COMPARATIVE EXAMPLE 7-b

A reaction was carried out in the same manner as in Comparative Example 3-b except that the reaction time was changed to 4,000 hours. The results are shown in Table 1-b.

It is appreciated from the results of Table 1-b that in Comparative Example 7-b, as compared with Example 3-b, activity reduction and yield reduction are both large and the catalyst has a problem in stability.

EXAMPLE 4-b

A reaction was carried out in the same manner as in Example 2-b except that the reaction temperature was changed to 360° C. and the space velocity was changed to 3,000 $hu^{-1}$ (STP). The results are shown in Table 1-b.

EXAMPLE 8-b

A reaction was carried out in the same manner as in Comparative Example 4-b except that the reaction temperature was changed to 360° C. and the space velocity was changed to 3,000 $hu^{-1}$ (STP). The results are shown in Table 1-b.

COMPARATIVE EXAMPLE 9-b

A reaction was carried out in the same manner as in Comparative Example 6-b except that the reaction temperature was changed to 360° C. and the space velocity was changed to 3,000 $hu^{-1}$ (STP). The results are shown in Table 1-b.

It is appreciated from the results of Example 4-b and Comparative Examples 8-b and 9-b that the superiority in activity and yield, of the catalyst system of the present invention using the catalysts (1-b) and (2-b) in combination, over the catalyst (1-b) or (3-b) appears even when space velocity is increased.

EXAMPLE 5-b

A reaction was carried out in the same manner as in Example 2-b except that the proportions of isobutylene and nitrogen in material gas were changed to 7% by volume and 69.8% by volume, respectively. The results are shown in Table 1-b.

COMPARATIVE EXAMPLE 10-b

A reaction was carried out in the same manner as in Example 4-b except that the proportions of isobutylene and nitrogen in material gas were changed to 7% by volume and 69.8% by volume, respectively. The results are shown in Table 1-b.

COMPARATIVE EXAMPLE 11-b

A reaction was carried out in the same manner as in Example 6-b except that the proportions of isobutylene and nitrogen in material gas were changed to 7% by volume and 69.8% by volume, respectively. The results are shown in Table 1-b.

It is appreciated from the results of Example 5-b and Comparative Examples 10-b and 11-b that the superiority in yield and ΔT, of the catalyst system of the present invention using the catalysts (1-b) and (2-b) in combination, over the catalyst (1-b) or (3-b) appears even when isobutylene concentration is increased. The present catalyst system, as compared with the single use of the catalyst (1-b) or (3-b), gives a considerably small increase in ΔT of catalyst layer, in particular. Therefore, it is thought that catalyst arrangement as in the present invention is effective for minimization of catalyst deterioration caused by thermal load.

EXAMPLE 6-b

A reaction was carried out in the same manner as in Example 1-b except that isobutylene was replaced by t-butanol. The results are shown in Table 2-b.

COMPARATIVE EXAMPLE 12-b

A reaction was carried out in the same manner as in Comparative Example 1-b except that isobutylene was replaced by t-butanol. The results are shown in Table 2-b.

COMPARATIVE EXAMPLE 13-b

A reaction was carried out in the same manner as in Comparative Example 3-b except that isobutylene was replaced by t-butanol. The results are shown in Table 2-b.

EXAMPLE 8-b

A reaction was carried out in the same manner as in Example 2-b except that there was used a material gas consisting of 5% by volume of methyl t-butyl ether (MTBE), 13.2% by volume of oxygen, 10% by volume of steam and 71.8% by volume of nitrogen, the reaction temperature was changed to 360° C. and the space velocity was changed to 1,000 hu$^{-1}$ (STP). The results are shown in Table 3-b.

COMPARATIVE EXAMPLE 14-b

A reaction was carried out in the same manner as in Comparative Example 4-b except that there was used a material gas consisting of 5% by volume of MTBE, 13.2% by volume of oxygen, 10% by volume of steam and 71.8% by volume of nitrogen, the reaction temperature was changed to 360° C. and the space velocity was changed to 1,000 hr$^{-1}$ (STP). The results are shown in Table 3-b.

COMPARATIVE EXAMPLE 15-b

A reaction was carried out in the same manner as in Comparative Example 6-b except that there was used a material gas consisting of 5% by volume of MTBE, 13.2% by volume of oxygen, 10% by volume of steam and 71.8% by volume of nitrogen, the reaction temperature was changed to 360° C. and the space velocity was changed to 1,000 hr$^{-1}$ (STP). The results are shown in Table 3-b.

EXAMPLE 8-b

A catalyst (4-b) was prepared in the same manner as in Example 1-b except that cobalt nitrate was replaced by nickel nitrate, phosphoric acid was added after ammonium paratungstate, there were used thallous nitrate and strontium nitrate in place of cesium nitrate and barium nitrate, then stannic oxide was added, and silica sol was replaced by ammonium nitrate.

The catalyst (4-b) had the following composition in terms of atomic ratio excluding oxygen.

$$Mo_{12}W_2Bi_3Fe_1Ni_7Tl_{0.6}Sr_{0.1}P_{0.2}Sn_{0.5}Al_1$$

A catalyst (5-b) was prepared in the same manner as for the catalyst (4-b) except that the amount of strontium nitrate used was changed.

The catalyst (5-b) had the following composition in terms of atomic ratio excluding oxygen.

$$Mo_{12}W_2Bi_3Fe_1Ni_7Tl_{0.6}Sr_{0.5}P_{0.2}Sn_{0.5}Al_1$$

750 ml of the catalyst (4-b) was filled into the gas inlet side of a steel-made reaction tube of 25.4 mm in diameter, and 750 ml of the catalyst (5-b) was filled into the gas outlet side.

A reaction was carried out in the same manner as in Example 1-b. The results are shown in Table 4-b.

COMPARATIVE EXAMPLE 16-b

A reaction was carried out in the same manner as in Example 8-b except that no catalyst (5-b) was used and only the catalyst (4-b) (1,500 ml) was filled. The results are shown in Table 4-b.

COMPARATIVE EXAMPLE 17-b

A reaction was carried out in the same manner as in Example 8-b except that no catalyst (4-b) was used and only the catalyst (5-b) (1,500 ml) was filled. The results are shown in Table 4-b.

EXAMPLE 9-b

A catalyst (6-b) was obtained in the same manner as in Example 1-b except that no ammonium paratungstate was used, cesium nitrate was replaced by potassium nitrate and sodium nitrate, barium nitrate was replaced by calcium nitrate and beryllium nitrate, silica sol was replaced by titanium dioxide, and cerous nitrate and niobium pentoxide were used finally. The catalyst (6-b) had the following composition in terms of atomic ratio excluding oxygen.

$$Mo_{12}Bi_1Fe_1Co_6K_{0.8}Na_{0.2}Ca_{0.1}Be_{0.1}Nb_{0.5}Ce_1Ti_1$$

A catalyst (7-b) was prepared in the same manner as for the catalyst (6-b) except that the amounts of calcium nitrate and beryllium nitrate were changed. The catalyst (7-b) had the following composition in terms of atomic ratio excluding oxygen.

$$Mo_{12}Bi_1Fe_1Co_6K_{0.8}Na_{0.2}Ca_{0.7}Be_{0.3}Nb_{0.5}Ce_1Ti_1$$

750 ml of the catalyst (6-b) was filled into the gas inlet portion of a steel-made reaction tube of 25.4 mm in diameter, and 750 ml of the catalyst (7-b) was filled into the gas outlet portion.

A reaction was carried out in the same manner as in Example 1-b. The results are shown in Table 4-b.

COMPARATIVE EXAMPLE 18-b

A reaction was carried out in the same manner as in Example 9-b except that no catalyst (7-b) was used and only the catalyst (6-b) (1,500 ml) was filled. The results are shown in Table 4-b.

COMPARATIVE EXAMPLE 19-b

A reaction was carried out in the same manner as in Example 9-b except that no catalyst (6-b) was used and only the catalyst (7-b) (1,500 ml) was filled. The results are shown in Table 4-b.

EXAMPLE 10-b

A suspension was prepared in the same manner as in Example 1-b except that no ammonium paratungstate was used, cesium nitrate was replaced by rubidium nitrate, magnesium nitrate was used together with barium nitrate, then there were added tellurium dioxide, lead nitrate and zinc nitrate, and silica sol was replaced by titanium dioxide.

The suspension was stirred with heating and subjected to evaporation to dryness. The residue was molded into rings of 6 mm in outside diameter, 6.6 mm in length and 2 mm in inside diameter of through-hole, and fired at 500° C. for 6 hours in an air stream to obtain a catalyst (8-b). The catalyst (8-b) had the following composition in terms of atomic ratio excluding oxygen.

$$Mo_{12}Bi_1Fe_3Co_7Rb_{0.5}Ba_{0.1}Mg_{0.1}Te_{0.3}Pb_1Zn_{0.5}Ti_1$$

A catalyst (9-b) was obtained in the same manner as for the catalyst (8-b) except that the amounts of barium nitrate and magnesium nitrate were changed. The catalyst had the following composition in terms of atomic ratio excluding oxygen.

$$Mo_{12}Bi_1Fe_3Co_7Rb_{0.5}Ba_{0.2}Mg_{1.0}Te_{0.3}Pb_1Zn_{0.5}Ti_1$$

750 ml of the catalyst (8-b) was filled into the gas inlet side of a steel-made reactor of 25.4 mm in diameter, and 750 ml of the catalyst (9-b) was filled into the gas outlet side. A reaction was carried out in the same manner as in Example 1-b except that the reaction temperature was changed to 350° C. The results are shown in Table 4-b.

COMPARATIVE EXAMPLE 20-b

A reaction was carried out in the same manner as in Example 10-b except that no catalyst (9-b) was used and only the catalyst (8-b) (1,500 ml) was filled. The results are shown in Table 4-b.

COMPARATIVE EXAMPLE 21-b

A reaction was carried out in the same manner as in Example 10-b except that no catalyst (8-b) was used and only the catalyst (9-b) (1,500 ml) was filled. The results are shown in Table 4-b.

EXAMPLE 11-b

A suspension was prepared in the same manner as in Example 1-b except that lithium nitrate was used together with cesium nitrate, barium nitrate was replaced by calcium nitrate, then there were added antimony trioxide and manganese nitrate, and silica sol was replaced by zirconium nitrate.

Using the suspension, a catalyst (10-b) was prepared in the same manner as in Example 10-b. The catalyst (10-b) had the following composition in terms of atomic ratio excluding oxygen.

$$Mo_{12}W_{1.5}Bi_1Fe_{1.2}Co_5Cs_{0.4}Li_{0.1}Ca_{0.2}Sb_1Mn_{0.5}Zr_1$$

A catalyst (11-b) was prepared in the same manner as for the catalyst (10-b) except that calcium nitrate was replaced by magnesium nitrate. The catalyst (11-b) had the following composition in terms of atomic ratio excluding oxygen.

$$Mo_{12}W_{1.5}Bi_1Fe_{1.2}Co_5Cs_{0.4}Li_{0.1}Mg_{0.8}Sb_1Mn_{0.5}Zr_1$$

750 ml of the catalyst (10-b) was filled into the gas inlet portion of a steel-made reaction tube of 25.4 mm in diameter, and 750 ml of the catalyst (11-b) was filled into the gas outlet side.

A reaction was carried out in the same manner as in Example 1-b. The results are shown in Table 4-b.

COMPARATIVE EXAMPLE 22-b

A reaction was carried out in the same manner as in Example 11-b except that no catalyst (11-b) was used and only the catalyst (10-b) (1,500 ml) was filled. The results are shown in Table 4-b.

COMPARATIVE EXAMPLE 23-b

A reaction was carried out in the same manner as in Example 11-b except that no catalyst (10-b) was used and only the catalyst (11-b) (1,500 ml) was filled. The results are shown in Table 4-b.

TABLE 1-b

| | | (Reaction conditions) | | | | | |
|---|---|---|---|---|---|---|---|
| | Method of catalyst filling Inlet portion/Outlet portion | Reaction temperature (°C.) | ΔT (°C.) | Isobutylene conversion (mole %) | Selectivity (mole %) | | Total per-pass yield (mole %) |
| | | | | | Methacrolein | Methacrylic acid | |
| Example 1-b | Catalyst (1-b) Pellets/catalyst (2-b) pellets | 340 | 71 | 98.8 | 85.2 | 3.5 | 87.6 |
| Comparative Example | | | | | | | |
| 1-b | Single layer of catalyst (1-b) pellets | 340 | 72 | 95.3 | 85.4 | 3.2 | 84.4 |
| 2-b | Single layer of catalyst (2-b) pellets | 340 | 94 | 99.1 | 79.0 | 5.2 | 83.4 |
| 3-b | Single layer of catalyst (3-b) pellets | 340 | 86 | 98.0 | 83.9 | 3.4 | 85.6 |
| Example 2-b | Catalyst (1-b) rings/catalyst (2-b) rings | 340 | 63 | 99.1 | 86.6 | 2.9 | 88.7 |
| Comparative Example | | | | | | | |
| 4-b | Single layer of catalyst (1-b) rings | 340 | 63 | 95.7 | 86.6 | 2.9 | 85.7 |
| 5-b | Single layer of catalyst (2-b) rings | 340 | 85 | 99.4 | 81.1 | 4.7 | 85.3 |
| 6-b | Single layer of catalyst (3-b) rings | 340 | 78 | 98.7 | 85.3 | 3.1 | 87.3 |
| Example 3-b | Catalyst (1-b) pellets/catalyst (2-b) pellets | 340 | 52 | 98.1 | 86.0 | 3.1 | 87.4 |
| Comparative Example 7-b | Single layer of catalyst (3-b) rings | 340 | 66 | 94.1 | 84.4 | 3.4 | 82.6 |
| Example 4-b | Catalyst (1-b) rings/catalyst (2-b) rings | 360 | 64 | 98.7 | 86.2 | 2.9 | 87.9 |
| Comparative Example | | | | | | | |
| 8-b | Single layer of catalyst (1-b) rings | 360 | 65 | 94.3 | 85.7 | 3.0 | 83.6 |
| 9-b | Single layer of catalyst (2-b) rings | 360 | 82 | 97.5 | 84.6 | 3.2 | 85.6 |
| Example 5-b | Catalyst (1-b) rings/catalyst (2-b) rings | 340 | 67 | 99.3 | 85.9 | 3.0 | 88.3 |
| Comparative Example | | | | | | | |
| 10-b | Single layer of catalyst (1-b) rings | 340 | 67 | 96.2 | 85.7 | 3.1 | 85.4 |

TABLE 1-b-continued

| | Method of catalyst filling Inlet portion/Outlet portion | (Reaction conditions) Reaction temperature (°C.) | ΔT (°C.) | Isobutylene conversion (mole %) | Selectivity (mole %) | | Total per-pass yield (mole %) |
|---|---|---|---|---|---|---|---|
| | | | | | Methacrolein | Methacrylic acid | |
| 11-b | Single layer of catalyst (3-b) rings | 340 | 83 | 99.1 | 83.6 | 3.3 | 86.1 |

Notes:
Example 3-b, Comparative Example 7-b = after 4,000 hours of continuous operation
Example 4-b, Comparative Examples 8-b and 9-b = space velocity 1,600→3,000 hr$^{-1}$ (STP)
Example 5-b, Comparative Examples 11-b and 11-b = isobutylene concentration 6→7% by volume TABLE 2-b

| | Method of catalyst filling Inlet portion/Outlet portion | (Reaction conditions) Reaction temperature (°C.) | ΔT (°C.) | t-Butanol conversion (mole %) | Per-pass yield (mole %) | | Total per-pass yield (mole %) |
|---|---|---|---|---|---|---|---|
| | | | | | Methacrolein | Methacrylic acid | |
| Example 6-b | Catalyst (1-b) pellets/catalyst (2-b) pellets | 340 | 63 | 100.0 | 84.7 | 3.2 | 87.9 |
| Comparative Example | | | | | | | |
| 12-b | Single layer of catalyst (1-b) pellets | 340 | 63 | 100.0 | 82.3 | 2.9 | 85.2 |
| 13-b | Single layer of catalyst (3-b) pellets | 340 | 76 | 100.0 | 83.2 | 3.1 | 86.3 |

TABLE 3-b

| | Method of catalyst filling Inlet portion/Outlet portion | (Reaction conditions) Reaction temperature (°C.) | ΔT (°C.) | MTBE conversion (mole %) | Selectivity (mole %) | | Total per-pass yield (mole %) |
|---|---|---|---|---|---|---|---|
| | | | | | Methacrolein | Methacrylic acid | |
| Example 7-b | Catalyst (1-b) rings/catalyst (2-b) rings | 360 | 63 | 98.1 | 82.1 | 4.2 | 84.7 |
| Comparative Example | | | | | | | |
| 14-b | Single layer of catalyst (1-b) rings | 360 | 62 | 95.0 | 82.4 | 4.3 | 82.4 |
| 15-b | Single layer of catalyst (3-b) rings | 360 | 76 | 97.5 | 80.8 | 4.5 | 83.2 |

TABLE 4-b

| | Method of catalyst filling Inlet portion/Outlet portion | (Reaction conditions) Reaction temperature (°C.) | ΔT (°C.) | Isobutylene conversion (mole %) | Selectivity (mole %) | | Total per-pass yield (mole %) |
|---|---|---|---|---|---|---|---|
| | | | | | Methacrolein | Methacrylic acid | |
| Example 8-b | Catalyst (4-b) Pellets/catalyst (5-b) pellets | 340 | 66 | 98.2 | 84.3 | 3.2 | 85.9 |
| Comparative Example | | | | | | | |
| 16-b | Single layer of catalyst (4-b) pellets | 340 | 66 | 94.2 | 84.5 | 3.0 | 82.4 |
| 17-b | Single layer of catalyst (5-b) pellets | 340 | 91 | 98.7 | 77.6 | 5.0 | 81.5 |
| Example 9-b | Catalyst (6-b) pellets/catalyst (7-b) pellets | 340 | 65 | 96.3 | 82.9 | 3.0 | 82.7 |
| Comparative Example | | | | | | | |
| 18-b | Single layer of catalyst (6-b) pellets | 340 | 64 | 92.1 | 83.1 | 2.6 | 78.9 |
| 19-b | Single layer of catalyst (7-b) pellets | 340 | 93 | 97.0 | 76.6 | 4.8 | 79.0 |
| Example 10-b | Catalyst (8-a) rings/catalyst (9-b) ringss | 340 | 60 | 97.2 | 85.7 | 2.9 | 86.1 |
| Comparative Example | | | | | | | |
| 20-b | Single layer of catalyst (8-b) rings | 340 | 61 | 93.7 | 85.6 | 2.8 | 82.8 |
| 21-b | Single layer of catalyst (9-b) rings | 340 | 82 | 97.5 | 79.9 | 4.8 | 82.6 |
| Example 11-b | Catalyst (10-b) rings/catalyst (11-b) rings | 340 | 59 | 98.1 | 83.9 | 2.9 | 85.2 |
| Comparative Example | | | | | | | |
| 22-b | Single layer of catalyst (10-b) rings | 340 | 59 | 93.4 | 84.1 | 2.5 | 80.9 |
| 23-b | Single layer of catalyst (11-b) rings | 340 | 79 | 98.5 | 77.7 | 4.0 | 80.5 |

EXAMPLE 1-c 1,456 g of cobalt nitrate and 202 g of ferric nitrate were dissolved in 1,000 ml of water. 243 g of bismuth nitrate was dissolved in an aqueous nitric acid solution consisting of 30 ml of concentrated nitric acid and 120 ml of water.

Separately, 1,059 g of ammonium paramolybdate and 265 g of ammonium paratungstate were dissolved in 3,000 ml of water being stirred with heating. To the resulting aqueous solution were dropwise added the above prepared two aqueous solutions, and mixing was carried out. Thereto were added an aqueous solution obtained by dissolving 9.8 g of cesium nitrate in 30 ml of water, 79.8 g of tellurium dioxide and 203 g of silica sol of 20 weight % concentration in this order, and mixing was carried out.

The thus obtained suspension was stirred with heating, and subjected to evaporation to dryness. The residue was molded into pellets of 6 mm in outside diameter and 6.6 mm in length. The pellets were fired at 500° C. for 6 hours in an air stream to obtain a catalyst (1-c). This catalyst (1-c) had the following composition in terms of atomic ratio excluding oxygen.

$$Mo_{12}W_2Bi_1Fe_1Co_{10}Cs_{0.1}Te_{1.0}Si_{1.35}$$

A catalyst (2-c) was prepared in the same manner as in the preparation of the catalyst (1-c) except that the amount of tellurium dioxide was changed to 8.0 g. This catalyst (2-c) had the following composition in terms of atomic ratio excluding oxygen.

$$Mo_{12}W_2Bi_1Fe_1Co_{10}Cs_{0.1}Te_{0.1}Si_{1.35}$$

With respect to the activities of the catalysts (1-c) and (2-c), the catalyst (2-c) has a higher activity than the catalyst (1-c), as is clear from the results of Comparative Examples 1-c and 2-c shown later.

750 ml of the catalyst (1-c) was filled into the material gas inlet portion of a steel-made reaction tube of 25.4 mm in diameter, and 750 ml of the catalyst (2-c) was filled into the material gas outlet portion.

A mixed gas of a composition consisting of 6% by volume of isobutylene, 13.2% by volume of oxygen, 10% by volume of steam and 70.8% by volume of nitrogen was introduced from the inlet of the reaction tube, and a reaction was carried out at a reaction temperature of 340° C. at a space velocity (SV) of 1,600 hu$^{-1}$(STP). The results are shown in Table 1-c.

COMPARATIVE EXAMPLE 1-c

A reaction was carried out in the same manner as in Example 1-c except that no catalyst (2-c) was used and only the catalyst (1-c) (1,500 ml) was filled into the reaction tube. The results are shown in Table 1-c.

COMPARATIVE EXAMPLE 2-c

A reaction was carried out in the same manner as in Example 1-c except that no catalyst (1-c) was used and only the catalyst (2-c) (1,500 ml) was filled into the reaction tube. The results are shown in Table 1-c.

COMPARATIVE EXAMPLE 3-c

A catalyst (3-c) was prepared in the same manner as for the catalyst (1-c) except that the amount of tellurium dioxide used was changed to 43.9 g.

The catalyst (3-c) had the following composition in terms of atomic ratio excluding oxygen.

$$Mo_{12}W_2Bi_1Fe_1Co_{10}Cs_{0.1}Te_{0.55}Si_{1.35}$$

A reaction was carried out in the same manner as in Example 1-c except that only the catalyst (3-c) (1,500 ml) was filled into the reaction tube. The results are shown in Table 1-c.

It is appreciated from the results of Table 1-c that the catalyst (1-c) has a very low activity, the catalyst (2-c) has a high activity but a low selectivity, and both of them give a low total per-pass yield while the catalyst system of the present invention which is a combination of the catalysts (1-c) and (2-c), gives a high total per-pass yield and produces intended methacrolein and methacrylic acid at high yields.

When the catalyst (3-c) having a composition intermediate between those of the catalysts (1-c) and (2-c) is compared with the catalyst system of the present invention which is a combination of the catalysts (1-c) and (2-c), the catalyst (3-c) gives a low total per-pass yield and a very large temperature difference (a very large ΔT) between the reaction temperature and the highest temperature in catalyst layer. Therefore, it is thought that catalyst deterioration due to thermal load is striking in the catalyst (3-c). Accordingly, it is appreciated that the single use of the catalyst (3-c) having substantially the same composition as the present catalyst system is unable to achieve the effect of the present invention. It can be said from these matters that the catalyst system of the present invention is very superior in both per-pass yield and thermal load.

EXAMPLE 2-c

A reaction was carried out in the same manner as in Example 1-c except that both of the catalysts (1-c) and (2-c) were molded into rings of 6 mm in outside diameter, 6.6 mm in length and 1 mm in inside diameter of through-hole. The results are shown in Table 1-c.

COMPARATIVE EXAMPLE 4-c

A reaction was carried out in the same manner as in Comparative Example 1-c except that the catalyst (1-c) was molded into rings of 6 mm in outside diameter, 6.6 mm in length and 1 mm in inside diameter of through-hole. The results are shown in Table 1-c.

COMPARATIVE EXAMPLE 5-c

A reaction was carried out in the same manner as in Comparative Example 2-c except that the catalyst (2-c) was molded into rings of 6 mm in outside diameter, 6.6 mm in length and 1 mm in inside diameter of through-hole. The results are shown in Table 1-c.

COMPARATIVE EXAMPLE 6-c

A reaction was carried out in the same manner as in Comparative Example 3-c except that the catalyst (3-c) was molded into rings of 6 mm in outside diameter, 6.6 mm in length and 1 mm in inside diameter of through-hole. The results are shown in Table 1-c.

In Example 2-c and Comparative Examples 4-c to 6-c, the shapes of the catalysts (1-c) to (3-c) were changed from pellets to rings. It is appreciated from the results of Table 1-c that the change of catalyst shape to rings gives improvement in yield and reduction in ΔT in all of the catalysts (1-c) to (3-c), but the catalyst system of the present invention using the catalysts (1-c) and (2-c) in combination gives a higher yield and a lower ΔT than the single use of the catalyst (1-c), (2-c) or (3-c).

EXAMPLE 3-c

A reaction was carried out in the same manner as in Example 1-c except that the catalyst (1-c) was molded into rings of 6.0 mm in outside diameter, 6.6 mm in length and 1.9 mm in inside diameter of through-hole. The results are shown in Table 1-c.

It was found that the change of the catalyst filled into the inlet portion of the reaction tube, from pellet shape to ring shape gives further improvement in per-pass yield and reduction in ΔT and accordingly the combination of ring-shaped catalysts gives superior results than the combination of pellet-shaped catalysts.

EXAMPLE 4-c

A reaction was carried out in the same manner as in Example 1-c except that the reaction was carried out for an extended period of time up to 4,000 hours. The results are shown in Table 1-c.

It is appreciated from the results of Table 1-c that activity reduction is very low even after the reaction of 4,000 hours, yield reduction is substantially negligible, and the catalyst system of the present invention enables very stable operation over a long period of time.

COMPARATIVE EXAMPLE 7-c

A reaction was carried out in the same manner as in Comparative Example 3-c except that the reaction time was changed to 4,000 hours. The results are shown in Table 1-c.

It is appreciated from the results of Table 1-c that in Comparative Example 7-c, as compared with Example 4-c, activity reduction and yield reduction are both large and the catalyst has a problem in stability.

EXAMPLE 5-c

A reaction was carried out in the same manner as in Example 2-c except that the reaction temperature was changed to 360° C. and the space velocity was changed to 3,000 hr$^{-1}$ (STP). The results are shown in Table 1-c.

EXAMPLE 8-c

A reaction was carried out in the same manner as in Comparative Example 4-c except that the reaction temperature was changed to 360° C. and the space velocity was changed to 3,000 hr$^{-1}$ (STP). The results are shown in Table 1-c.

COMPARATIVE EXAMPLE 9-c

A reaction was carried out in the same manner as in Comparative Example 6-c except that the reaction temperature was changed to 360° C. and the space velocity was changed to 3,000 hu$^{-1}$ (STP). The results are shown in Table 1-c.

It is appreciated from the results of Example 5-c and Comparative Examples 8-c and 9-c that the superiority in activity and yield, of the catalyst system of the present invention using the catalysts (1-c) and (2-c) in combination, over the catalyst (1-c) or (3-c) appears even when space velocity is increased.

EXAMPLE 6-c

A reaction was carried out in the same manner as in Example 2-c except that the proportions of isobutylene and nitrogen in material gas were changed to 7% by volume and 69.8% by volume, respectively. The results are shown in Table 1-c.

COMPARATIVE EXAMPLE 10-c

A reaction was carried out in the same manner as in Example 4-c except that the proportions of isobutylene and nitrogen in material gas were changed to 7% by volume and 69.8% by volume, respectively. The results are shown in Table 1-c.

COMPARATIVE EXAMPLE 11-c

A reaction was carried out in the same manner as in Example 6-c except that the proportions of isobutylene and nitrogen in material gas were changed to 7% by volume and 69.8% by volume, respectively. The results are shown in Table 1-c.

It is appreciated from the results of Example 6-c and Comparative Examples 10-c and 11-c that the superiority in yield and ΔT, of the catalyst system of the present invention using the catalysts (1-c) and (2-c) in combination, over the catalyst (1-c) or (3-c) appears even when isobutylene concentration is increased. The present catalyst system, as compared with the single use of the catalyst (1-c) or (3-c), gives a considerable small increase in ΔT of catalyst layer, in particular. Therefore, it is thought that catalyst arrangement as in the present invention is effective for minimization of catalyst deterioration caused by thermal load.

EXAMPLE 7-c

A reaction was carried out in the same manner as in Example 2-c except that isobutylene was replaced by t-butanol. The results are shown in Table 2-c.

COMPARATIVE EXAMPLE 12-c

A reaction was carried out in the same manner as in Comparative Example 4-c except that isobutylene was replaced by t-butanol. The results are shown in Table 2-c.

COMPARATIVE EXAMPLE 13-c

A reaction was carried out in the same manner as in Comparative Example 6-c except that isobutylene was replaced by t-butanol. The results are shown in Table 2-c.

EXAMPLE 8-c

A reaction was carried out in the same manner as in Example 2-c except that there was used a material gas consisting of 5% by volume of methyl t-butyl ether (MTBE), 13.2% by volume of oxygen, 10% by volume of steam and 71.8% by volume of nitrogen, the reaction temperature was changed to 360° C. and the space velocity was changed to 1,000 hu$^{-1}$ (STP). The results are shown in Table 3-c.

COMPARATIVE EXAMPLE 14-c

A reaction was carried out in the same manner as in Comparative Example 4-c except that there was used a material gas consisting of 5% by volume of MTBE, 13.2% by volume of oxygen, 10% by volume of steam and 71.8% by volume of nitrogen, the reaction temperature was changed to 360° C. and the space velocity was changed to 1,000 hr$^{-1}$ (STP). The results are shown in Table 3-c.

COMPARATIVE EXAMPLE 15-c

A reaction was carried out in the same manner as in Comparative Example 6-c except that there was used a material gas consisting of 5% by volume of MTBE, 13.2% by volume of oxygen, 10% by volume of steam and 71.8% by volume of nitrogen, the reaction temperature was changed to 360° C. and the space velocity was changed to 1,000 hr$^{-1}$ (STP). The results are shown in Table 3-c.

EXAMPLE 9-c

A suspension was prepared in the same manner as in Example 1-c except that cobalt nitrate was replaced by nickel nitrate, the amount of bismuth nitrate used was changed, cesium nitrate was replaced by rubidium nitrate and magnesium nitrate, then stannic oxide was added in place of tellurium dioxide, and aluminum nitrate was used in addition to silica sol. The suspension was subjected to the same procedure as in Example 2-c to prepare a ring-shaped catalyst (4-c).

The catalyst (4-c) had the following composition in terms of atomic ratio excluding oxygen.

$Mo_{12}W_2Bi_{1.2}Fe_1Ni_7Rb_{0.1}Mg_{0.5}Sn_{1.0}Al_{1.0}Si_{1.35}$

A suspension was prepared in the same manner as for the catalyst (4-c) except that the amounts of stannic oxide and silica sol used were changed. The suspension was subjected to the same procedure as in Example 1-c to prepare a pellet-shaped catalyst (5-c).

The catalyst (5-c) had the following composition in terms of atomic ratio excluding oxygen.

$Mo_{12}W_2Bi_{2.0}Fe_1Ni_7Rb_{0.1}Mg_{0.5}Sn_{0.1}Al_{1.0}Si_{0.5}$ 750 ml of the catalyst (4-c) was filled into the gas inlet side of a steel-made reaction tube of 25.4 mm in diameter, and 750 ml of the catalyst (5-c) was filled into the gas outlet side.

A reaction was carried out in the same manner as in Example 1-c. The results are shown in Table 4-c.

EXAMPLE 10-c

A suspension was prepared in the same manner as in Example 1-c except that the amount of cobalt nitrate used was changed, thallous nitrate, barium nitrate and cerous nitrate were used in addition to cesium nitrate, no tellurium dioxide was used, and silica sol was replaced by aluminum nitrate. The suspension was subjected to the same procedure as in Example 2-c to obtain a ring-shaped catalyst (6-c).

This catalyst (6-c) had the following composition in terms of atomic ratio excluding oxygen.

$Mo_{12}W_2Bi_1Fe_1Co_6Cs_{0.1}Tl_{0.2}Ba_{0.1}Ce_{0.2}Al_{2.0}$

A ring-shaped catalyst (7-c) was prepared in the same manner as for the catalyst (6-c) except that the amounts of ferric nitrate, cerous nitrate and aluminum nitrate used were changed. This catalyst (7-c) had the following composition in terms of atomic ratio excluding oxygen.

$Mo_{12}W_2Bi_1Fe_{1.4}Co_6Cs_{0.1}Tl_{0.2}Ba_{0.1}Ce_1Al_{2.0}$ 750 ml of the catalyst (6-c) was filled into the gas inlet side of a steel-made reaction tube 25.4 mm in diameter, and 750 ml of the catalyst (7-c) was filled into the gas outlet side.

A reaction was carried out in the same manner as in Example 1-c. The results are shown in Table 4-c.

EXAMPLE 11-c

A suspension was prepared in the same manner as in Example 1-c except that the amount of cobalt nitrate used was changed, cesium nitrate was replaced by potassium nitrate, lithium nitrate and beryllium nitrate, titanium oxide was used in place of tellurium and silica sol, and manganese nitrate was used finally.

In this suspension was immersed 1,600 ml of a spherical carrier of 6 mm in diameter, consisting of α-alumina. The system was heated to a predetermined temperature with stirring, whereby the carrier was allowed to support the catalyst composition.

The resulting supported catalyst was fired at 500° C. for 6 hours in an air stream to obtain a catalyst (8c).

The supported oxide catalyst (8-c) had the following composition in terms of atomic ratio excluding oxygen.

$Mo_{12}W_2Bi_1Fe_1Co_3K_{0.2}Li_{1.5}Be_{0.2}Mn_{2.0}Ti_{3.0}$

The amount of the supported oxide was 20 g per 100 ml of the carrier.

A suspension was prepared in the same manner as for the catalyst (8-c) except that the amounts of cobalt nitrate and titanium dioxide were changed and manganese nitrate was replaced by phosphorus. The suspension was subjected to the same procedure as in Example 1-c to obtain a pellet-shaped catalyst (9-c).

The catalyst (9-c) had the following composition in terms of atomic ratio excluding oxygen.

$Mo_{12}W_2Bi_1Fe_1Co_6K_{0.2}Li_{1.5}Be_{0.2}P_{0.2}Ti_{1.0}$ 900 ml of the catalyst (8-C) was filled into the gas inlet side of a steel-made reactor of 25.4 mm in diameter, and 600 ml of the catalyst (9-c) was filled into the gas outlet side. A reaction was carried out in the same manner as in Example 1-c except that the reaction temperature was changed to 350° C. The results are shown in Table 4-c.

EXAMPLE 12-c

A suspension was prepared in the same manner as in Example 1-c except that the amounts of ammonium paratungstate, ferric nitrate and cobalt nitrate were changed, calcium nitrate was used in addition to cesium nitrate, then zinc nitrate was added, and zirconium nitrate was used in place of tellurium dioxide and silica sol.

There were measured 1,600 ml of a ring-shaped carrier of 6 mm in outside diameter, 5 mm in length and 3 mm in inside diameter of through-hole, consisting of silica-alumina. Using this carrier, a supported catalyst (10-c) was prepared in the same manner as for the catalyst (8-c) of Example 11-c.

The catalyst (10-c) had the following composition in terms of atomic ratio excluding oxygen.

$Mo_{12}W_1Bi_1Fe_{1.2}Co_5Cs_{0.1}Ca_{0.3}Zn_{1.0}Zr_{2.0}$

The amount of the supported oxide was 24 g per 100 ml of the carrier.

A suspension was prepared in the same manner as for the catalyst (10-c) except that the amounts of ammonium paratungstate, bismuth nitrate, zinc nitrate and zirconium nitrate used were changed. Using this suspension, a ring-shaped catalyst (11-c) was obtained in the same manner as in Example 2-c.

The catalyst (11-c) had the following composition in terms of atomic ratio excluding oxygen.

$Mo_{12}W_1Bi_{1.4}Fe_{1.2}Co_5Cs_{0.1}Ca_{0.3}Zn_{1.2}Zr_{1.7}$ 1,000 ml of the catalyst (10-c) was filled into the gas inlet side of a steel-made reaction tube of 25.4 mm in diameter, and 500 ml of the catalyst (11-c) was filled into the gas outlet side. A reaction was carried out in the same manner as in Example 1-c except that the reaction temperature was changed to 350° C. The results are shown in Table 4-c.

EXAMPLE 13-c

A catalyst (12-c) was prepared in the same manner as in Example 1-c except that the amounts of ammonium paratungstate and cobalt nitrate were changed, sodium nitrate was used in addition to cesium nitrate, then lead nitrate and tellurium dioxide were added, and firing was carried out at 530° C. for 6 hours in an air stream.

The catalyst (12-c) had the following composition in terms of atomic ratio excluding oxygen.

$Mo_{12}W_{1.5}Bi_1Fe_1Co_7Cs_{0.1}Na_{1.0}Pb_{0.1}Te_{1.0}Si_{1.35}$

A catalyst (13-c) was prepared in the same manner as for the catalyst (12-c) except that the amounts of lead nitrate and tellurium dioxide were changed, antimony trioxide was used, and firing was carried out at 450° C.

The catalyst (13-c) had the following composition in terms of atomic ratio excluding oxygen.

$Mo_{12}W_{1.5}Bi_1Fe_1Co_7Cs_{0.1}Na_{1.0}Pb_{1.0}Te_{0.2}Sb_{0.1}Si_{1.35}$ 750 ml of the catalyst (12-c) was filled into the gas inlet side of a steel-made reaction tube of 25.4 mm in diameter, and 750 ml of the catalyst (13-c) was filled into the gas outlet side. A reaction was carried out in the same manner as in Example 1-c. The results are shown in Table 4-c.

EXAMPLE 14-c

A suspension was prepared in the same manner as in Example 1-c except that cobalt nitrate was replaced by nickel nitrate, cesium nitrate was replaced by rubidium nitrate and strontium nitrate, the amount of tellurium dioxide was changed, and niobium pentoxide was used. The suspension was subjected to evaporation to dryness. The residue was molded into rings of 6 mm in outside diameter, 6.6 mm in length and 2.0 mm in inside diameter of through-hole, and fired at 550° C. for 6 hours in an air stream to prepare a catalyst (14-c).

The catalyst (14-c) had the following composition in terms of atomic ratio excluding oxygen.

$Mo_{12}W_2Bi_1Fe_1Ni_3Rb_{0.8}Sr_{0.1}Te_{0.8}Nb_{0.2}Si_{1.35}$

A ring-shaped catalyst (15-c) was obtained in the same manner as for the catalyst (14-c) except that the amounts of ammonium paratungstate, ferric nitrate, nickel nitrate, telurium dioxide and niobium pentoxide were changed, and the firing temperature was changed to 470° C.

The catalyst (15-c) had the following composition in terms of atomic ratio excluding oxygen.

$Mo_{12}W_{2.4}Bi_1Fe_{1.2}Ni_7Rb_{0.8}Sr_{0.1}Te_{0.1}Nb_{0.2}Si_{1.35}$

A reaction was carried out in the same manner as in Example 1-c. The results are shown in Table 4-c.

TABLE 1-c

| | | (Reaction conditions) | | | | | |
|---|---|---|---|---|---|---|---|
| | Method of catalyst filling Inlet portion/Outlet portion | Reaction temperature (°C.) | ΔT (°C.) | Isobutylene conversion (mole %) | Selectivity (mole %) | | Total per-pass yield (mole %) |
| | | | | | Methacrolein | Methacrylic acid | |
| Example 1-c | Catalyst (1-c) Pellets/catalyst (2-c) pellets | 340 | 71 | 98.9 | 84.9 | 3.6 | 87.5 |
| Comparative Example | | | | | | | |
| 1-c | Single layer of catalyst (1-c) pellets | 340 | 71 | 95.4 | 85.0 | 3.2 | 84.1 |
| 2-c | Single layer of catalyst (2-b) pellets | 340 | 95 | 99.3 | 78.7 | 5.3 | 83.4 |
| 3-c | Single layer of catalyst (3-c) pellets | 340 | 88 | 98.1 | 83.5 | 3.4 | 85.2 |
| Example 2-c | Catalyst (1-c) rings/catalyst (2-c) rings | 340 | 62 | 99.2 | 86.3 | 3.1 | 88.7 |
| Comparative Example | | | | | | | |
| 4-c | Single layer of catalyst (1-c) rings | 340 | 61 | 95.9 | 86.3 | 3.1 | 85.7 |
| 5-c | Single layer of catalyst (2-c) rings | 340 | 84 | 99.5 | 80.8 | 5.0 | 85.4 |
| 6-c | Single layer of catalyst (3-c) rings | 340 | 77 | 98.9 | 85.0 | 3.4 | 87.4 |
| Example 3-c | Catalyst (1-c) rings/catalyst (2-c) pellets | 340 | 63 | 99.0 | 86.1 | 3.3 | 88.5 |
| 4-c | Catalyst (1-c) rings/catalyst (2-c) pellets | 340 | 41 | 98.1 | 86.6 | 3.0 | 87.9 |
| Comparative Example 7-c | Single layer of catalyst (3-c) pellets | 340 | 67 | 94.2 | 84.2 | 3.5 | 82.6 |
| Example 5-c | Catalyst (1-c) rings/catalyst (2-c) rings | 360 | 64 | 98.4 | 86.0 | 3.2 | 87.8 |
| Comparative Example | | | | | | | |
| 8-c | Single layer of catalyst (1-c) rings | 360 | 64 | 93.8 | 85.8 | 3.2 | 83.5 |
| 9-c | Single layer of catalyst (3-c) rings | 360 | 85 | 96.5 | 84.3 | 3.5 | 84.7 |
| Example 6-c | Catalyst (1-c) rings/catalyst (2-c) rings | 340 | 68 | 99.3 | 85.4 | 3.3 | 88.1 |

TABLE 1-c-continued

| | | (Reaction conditions) | | | Selectivity (mole %) | | Total per-pass yield (mole %) |
|---|---|---|---|---|---|---|---|
| | Method of catalyst filling Inlet portion/Outlet portion | Reaction temperature (°C.) | ΔT (°C.) | Isobutylene conversion (mole %) | Methacrolein | Methacrylic acid | |
| Comparative Example | | | | | | | |
| 10-c | Single layer of catalyst (1-c) rings | 340 | 68 | 96.1 | 85.3 | 3.3 | 85.1 |
| 11-c | Single layer of catalyst (3-c) rings | 340 | 82 | 99.1 | 83.4 | 3.6 | 86.2 |

Notes:
Example 4-c, Comparative Example 7-c = after 4,000 hours of continuous operation
Example 5-c, Comparative Examples 8-c and 9-c = space velocity 1,600 → 3,000 hr$^{-1}$ (STP)
Example 6-c, Comparative Examples 10-c and 11-c = isobutylene concentration 6 → 7% by volume TABLE 2-c

| | | (Reaction conditions) | | | Per-pass yield (mole %) | | Total per-pass yield (mole %) |
|---|---|---|---|---|---|---|---|
| | Method of catalyst filling Inlet portion/Outlet portion | Reaction temperature (°C.) | ΔT (°C.) | t-Butanol conversion (mole %) | Methacrolein | Methacrylic acid | |
| Example 7-c | Catalyst (1-c) rings/catalyst (2-c) rings | 340 | 54 | 100.0 | 85.5 | 2.9 | 88.4 |
| Comparative Example | | | | | | | |
| 12-c | Single layer of catalyst (1-c) rings | 340 | 54 | 100.0 | 82.2 | 3.0 | 85.2 |
| 13-c | Single layer of catalyst (3-c) rings | 340 | 72 | 100.0 | 83.6 | 3.4 | 87.0 |

TABLE 3-c

| | | (Reaction conditions) | | | Per-pass yield (mole %) | | Total per-pass yield (mole %) |
|---|---|---|---|---|---|---|---|
| | Method of catalyst filling Inlet portion/Outlet portion | Reaction temperature (°C.) | ΔT (°C.) | MTBE conversion (mole %) | Methacrolein | Methacrylic acid | |
| Example 8-c | Catalyst (1-c) rings/catalyst (2-c) rings | 360 | 64 | 98.0 | 81.5 | 4.7 | 84.5 |
| Comparative Example | | | | | | | |
| 14-c | Single layer of catalyst (1-c) rings | 360 | 63 | 94.8 | 81.8 | 4.8 | 82.1 |
| 15-c | Single layer of catalyst (3-c) rings | 360 | 78 | 97.4 | 80.5 | 4.9 | 83.2 |

TABLE 4-c

| | | (Reaction conditions) | | | Selectivity (mole %) | | Total per-pass yield (mole %) |
|---|---|---|---|---|---|---|---|
| | Method of catalyst filling Inlet portion/Outlet portion | Reaction temperature (°C.) | ΔT (°C.) | Isobutylene conversion (mole %) | Methacrolein | Methacrylic acid | |
| Example | | | | | | | |
| 9-c | Catalyst (4-c) rings/catalyst (5-c) pellets | 340 | 61 | 98.1 | 84.2 | 3.4 | 85.9 |
| 10-c | Catalyst (6-c) rings/catalyst (7-c) rings | 340 | 60 | 98.2 | 85.1 | 3.0 | 86.5 |
| 11-c | Catalyst (8-c) spheres supported on carrier/catalyst (9-c) pellets | 350 | 40 | 97.3 | 86.4 | 2.5 | 86.5 |
| 12-c | Catalyst (10-c) rings supported on carrier/catalyst (11-c) rings | 350 | 38 | 97.8 | 87.0 | 2.2 | 87.2 |
| 13-c | Catalyst (12-c) pellets/catalyst (13-c) pellets | 340 | 67 | 98.0 | 83.8 | 3.1 | 85.2 |
| 14-c | Catalyst (14-c) rings/catalyst (15-c) rings | 340 | 59 | 97.7 | 84.4 | 3.3 | 85.7 |

We claim:

1. A process for producing methacrolein and methacrylic acid by subjecting at least one material selected from isobutylene, t-butanol and methyl t-butyl ether to a gas phase catalytic oxidation with molecular oxygen or a molecular oxygen-containing gas using a fixed bed multi-tubular reactor, which process is characterized in that (i) there are used, as catalysts, compound oxides represented by the following general formula (I)

$$Mo_aW_bBi_cFe_dA_eB_fC_gD_hE_iO_x \qquad (I)$$

where Mo represents molybdenum, W represents tungsten, Bi represents bismuth, Fe represents iron, A represents at least one element selected from nickel and cobalt, B represents at least one element selected from alkali metals and thallium, C represents at least one element selected from alkaline earth metals, D represents at least one element selected from phosphorus, tellurium, antimony, tin, cerium, lead, niobium, manganese, arsenic and zinc, E represents at least one element selected from silicon, aluminum, titanium and zirconium, and O represents oxygen; a, b, c, d, e, f, g, h, i and x represent the numbers of atoms of Mo, W, Bi, Fe, A, B, C, D, E and O, respectively; wherein a is 12, b=0–10, c=0.1–20, d=0.1–20, e=2–20, f=0–10, g=0–10, h=0–4, i=0–30 and x=a value determined by the oxidation states of individual elements, (ii) each reaction tube has a plurality of reaction zones formed by dividing the catalyst layer in the reaction tube into two or more portions in the axial direction of the tube, and (iii) the plurality of reaction zones are filled with catalysts shown in the above (i) having different activities, prepared by varying the type(s) and/or amount(s) of the elements constituting the A group, B group, C group, D group and E group in the general formula (I) and/or with catalysts shown in the above (i) having different activities, prepared by varying the amount of at least one element of W, Bi and Fe in the general formula (I), in such a way that the activity of filled catalyst becomes higher as a material gas proceeds from the inlet to the outlet; wherein the catalysts are ring-shaped catalysts with a through-hole in the length direction, having an outside diameter of 3–10 mm, a length of 0.5–2 times the outside diameter and an inside diameter (the diameter of the through-hole) of 0.1–0.7 time the outside diameter, which further uses catalysts having different activities prepared by varying a firing temperature employed in catalyst preparation.

2. A process for producing methacrolein and methacrylic acid by subjecting t-butanol to a gas phase catalytic oxidation with molecular oxygen or a molecular oxygen-containing gas using a fixed bed multi-tubular reactor, which process is characterized in that:

(i) there are used, as catalysts, compound oxides represented by the following general formula (I)

$$Mo_aW_bBi_cFe_dA_eB_fC_gD_hE_iO_x \qquad (I)$$

which Mo represents molybdenum, W represents tungsten, Bi represents bismuth, Fe represents iron, A represents at least one element selected from nickel and cobalt, B represents at least one element selected from alkali metals and thallium, C represents at least one element selected from alkaline earth metals, D represents at least one element selected from phosphorus, tellurium, antimony, tin, cerium, lead, niobium, manganese, arsenic and zinc, E represents at least one element selected from silicon, aluminum, titanium and zirconium, and O represented oxygen; a, b, c, d, e, f, g, h, i and x represent the numbers of atoms of Mo, W, Bi, Fe, A, B, C, D, E and O, respectively;

wherein a is 12, b=0–10, c=0.1–20, d=0.1–20, e=-2–20, f=0–10, g=0–10, h=0–4, i=0–30 and x=a value determined by the oxidation states of individual elements, (ii) each reaction tube has a plurality of reaction zones formed by dividing the catalyst layer in the reaction tube into two or more portions in the axial direction of the tube, and (iii) the plurality of reaction zones are filled with catalysts shown in the above (i) having different activities, prepared by varying the type(s) or amount(s) of the elements in the general formula (I), in such a way that the activity of filled catalyst becomes higher as a material gas proceeds from the inlet to the outlet, which further uses catalysts having different activities prepared by varying a firing temperature employed in catalyst preparation.

3. A process for producing a methacrolein and methacrylic acid by subjecting methyl t-butyl ether to a gas phase catalytic oxidation with molecular oxygen or a molecular oxygen-containing gas using a fixed bed multi-tubular reactor, which process comprises:

(i) there are used, as catalysts, compound oxides represented by the following general formula (I)

$$Mo_aW_bBi_cFe_dA_eB_fC_gD_hE_iO_x \qquad (I)$$

where Mo represents molybdenum, W represents tungsten, Bi represents bismuth, Fe represents iron, A represents at least one element selected from nickel and cobalt, B represents at least one element selected from alkali metals and thallium, C represents at least one element selected from alkaline earth metals, D represents at least one element selected from phosphorus, tellurium, antimony, tin, cerium, lead, niobium, manganese, arsenic and zinc, E represents at least one element selected from silicon, aluminum, titanium and zirconium, and O represents oxygen, a, b, c, d, e, f, g, h, i and x represent the numbers of atoms of Mo, W, Bi, Fe, A, B, C, D, E and O, respectively; wherein a is 12, b=0–10, c=0.1–20, d=0.1–20, e=2–20, f=0–10, g=0–10, h=0–4, i=0–30 and x=a value determined by the oxidation states of individual elements, (ii) each reaction tube has a plurality of reaction zones formed by dividing the catalyst layer in the reaction tube into two or more portions in the axial direction of the tube, and (iii) the plurality of reaction zones are filled with catalysts shown in the above (i) having different activities, prepared by varying the type(s) or amount(s) of the elements in the general formula (I), in such a way that the activity of filled catalyst becomes higher as a material gas proceeds from the inlet to the outlet, which further uses catalysts having different activities prepared by varying a firing temperature employed in catalyst preparation.

* * * * *